(12) United States Patent
Christman et al.

(10) Patent No.: US 12,090,175 B2
(45) Date of Patent: Sep. 17, 2024

(54) COMPOSITIONS AND METHODS FOR TISSUE REPAIR WITH EXTRACELLULAR MATRICES

(71) Applicant: The Regents of the University of California, Oakland, CA (US)

(72) Inventors: Karen Christman, San Diego, CA (US); Jennifer Singelyn, Riverdale, NJ (US); Jessica DeQuach, La Jolla, CA (US)

(73) Assignee: The Regents of the University of California, Oakland, CA (US)

(*) Notice: Subject to any disclaimer, the term of this patent is extended or adjusted under 35 U.S.C. 154(b) by 932 days.

(21) Appl. No.: 17/135,785

(22) Filed: Dec. 28, 2020

(65) Prior Publication Data

US 2021/0260134 A1 Aug. 26, 2021

Related U.S. Application Data

(60) Continuation of application No. 13/891,562, filed on May 10, 2013, now abandoned, which is a division of
(Continued)

(51) Int. Cl.
*A61K 35/34* (2015.01)
*A61K 9/00* (2006.01)
(Continued)

(52) U.S. Cl.
CPC ............ *A61K 35/34* (2013.01); *A61K 9/0024* (2013.01); *A61L 27/3633* (2013.01);
(Continued)

(58) Field of Classification Search
CPC ..................................................... A61K 35/34
See application file for complete search history.

(56) References Cited

U.S. PATENT DOCUMENTS

| 4,902,508 A | 2/1990 | Badylak et al. |
| 4,956,178 A | 9/1990 | Badylak et al. |

(Continued)

FOREIGN PATENT DOCUMENTS

| CN | 1565649 A | 1/2005 |
| EP | 3000472 B1 | 4/2017 |

(Continued)

OTHER PUBLICATIONS

Bopassa et al. Abstract 27: Pae1 ituel Proteets Heart from Cold ischemia Through Inhibition of Mitochondrial Permeability Transition Pore (MPTP) Opening and Reduction of Myocardial Necrosis. Ciruclation. 2006; 114. p. 1.
(Continued)

*Primary Examiner* — Rosanne Kosson
(74) *Attorney, Agent, or Firm* — Eversheds Sutherland (US) LLP

(57) ABSTRACT

Described herein are compositions comprising decellularized cardiac extracellular matrix and therapeutic uses thereof. Methods for treating, repairing or regenerating defective, diseased, damaged or ischemic cells, tissues or organs in a subject, preferably a human, using a decellularized cardiac extracellular matrix of the invention are provided. Methods of preparing cardiomyocyte culture surfaces and culturing cells with absorbed decellularized cardiac extracellular matrix are provided.

13 Claims, 6 Drawing Sheets

Average Number of Cardiomyocytes

Related U.S. Application Data application No. 13/075,774, filed on Mar. 30, 2011, now abandoned, which is a continuation of application No. PCT/US2009/059015, filed on Sep. 30, 2009.

(60) Provisional application No. 61/101,332, filed on Sep. 30, 2008.

(51) Int. Cl.
*A61L 27/36* (2006.01)
*A61L 27/38* (2006.01)
*A61L 27/52* (2006.01)

(52) U.S. Cl.
CPC ........... *A61L 27/3834* (2013.01); *A61L 27/52* (2013.01); *A61L 2400/06* (2013.01); *A61L 2430/20* (2013.01)

(56) References Cited

U.S. PATENT DOCUMENTS

| | | | |
|---|---|---|---|
| 4,970,298 A | 11/1990 | Silver et al. | |
| 5,171,262 A | 12/1992 | MacGregor | |
| 5,275,826 A | 1/1994 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,516,533 A | 5/1996 | Badylak et al. | |
| 5,554,389 A | 9/1996 | Badylak et al. | |
| 5,573,784 A | 11/1996 | Badylak et al. | |
| 5,631,019 A | 5/1997 | Marx | |
| 5,645,860 A | 7/1997 | Knapp, Jr. et al. | |
| 5,665,391 A | 9/1997 | Lea et al. | |
| 5,711,969 A | 1/1998 | Patel et al. | |
| 5,741,701 A | 4/1998 | Swiderek et al. | |
| 5,753,267 A | 5/1998 | Badylak et al. | |
| 5,762,966 A | 6/1998 | Knapp, Jr. et al. | |
| 5,866,414 A | 2/1999 | Badylak et al. | |
| 5,885,619 A | 3/1999 | Patel et al. | |
| 5,955,110 A | 9/1999 | Patel et al. | |
| 5,968,096 A | 10/1999 | Whitson et al. | |
| 6,099,567 A | 8/2000 | Badylak et al. | |
| 6,187,039 B1 | 2/2001 | Hiles et al. | |
| 6,264,992 B1 | 7/2001 | Voytik-Harbin et al. | |
| 6,379,710 B1 | 4/2002 | Badylak | |
| 6,444,229 B2 | 9/2002 | Voytik-Harbin et al. | |
| 6,485,723 B1 | 11/2002 | Badylak et al. | |
| 6,551,618 B2 | 4/2003 | Baird et al. | |
| 6,554,857 B1 | 4/2003 | Zilla et al. | |
| 6,576,265 B1 | 6/2003 | Spievack | |
| 6,579,538 B1 | 6/2003 | Spievack | |
| 6,696,270 B2 | 2/2004 | Badylak et al. | |
| 6,783,776 B2 | 8/2004 | Spievack | |
| 6,793,939 B2 | 9/2004 | Badylak et al. | |
| 6,849,273 B2 | 2/2005 | Spievack | |
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 6,932,804 B2 | 8/2005 | Lee | |
| 7,235,295 B2 | 6/2007 | Laurencin et al. | |
| 7,252,819 B2 | 8/2007 | Lee | |
| 7,875,017 B2 | 1/2011 | Sabbah et al. | |
| 8,110,561 B2 | 2/2012 | Cohen et al. | |
| 8,168,612 B2 | 5/2012 | Cohen et al. | |
| 8,192,763 B2 | 6/2012 | Johnson | |
| 8,361,503 B2 | 1/2013 | Badylak et al. | |
| 8,691,276 B2 | 4/2014 | Badylak et al. | |
| 8,741,352 B2 | 6/2014 | Hodde et al. | |
| 8,802,436 B1 | 8/2014 | Kentner et al. | |
| 9,119,831 B2 | 9/2015 | Kentner et al. | |
| 9,205,172 B2 | 12/2015 | Neethling et al. | |
| 9,216,236 B2 | 12/2015 | Machluf et al. | |
| 9,238,091 B2 | 1/2016 | Kentner et al. | |
| 9,474,829 B2 | 10/2016 | Kentner et al. | |
| 9,795,713 B2 | 10/2017 | Kentner et al. | |
| 2001/0014475 A1 | 8/2001 | Frondoza et al. | |
| 2002/0085994 A1 | 7/2002 | Ceres et al. | |
| 2002/0090725 A1 | 7/2002 | Simpson et al. | |
| 2003/0012822 A1 | 1/2003 | Voytik-Harbin et al. | |
| 2003/0100944 A1 | 5/2003 | Laksin et al. | |
| 2004/0002740 A1 | 1/2004 | Lee | |
| 2004/0009600 A1 | 1/2004 | Bowlin et al. | |
| 2005/0003010 A1 | 1/2005 | Cohen et al. | |
| 2005/0013870 A1* | 1/2005 | Freyman | C12N 5/0679 435/325 |
| 2005/0013872 A1 | 1/2005 | Freyman et al. | |
| 2005/0181016 A1 | 8/2005 | Freyman et al. | |
| 2006/0134079 A1 | 6/2006 | Sih et al. | |
| 2006/0147433 A1 | 7/2006 | Hiles | |
| 2006/0149309 A1 | 7/2006 | Paul et al. | |
| 2006/0153815 A1 | 7/2006 | Seyda et al. | |
| 2007/0014755 A1 | 1/2007 | Beckman et al. | |
| 2007/0014773 A1 | 1/2007 | Matheny et al. | |
| 2007/0014870 A1 | 1/2007 | Matheny | |
| 2007/0014871 A1 | 1/2007 | Matheny et al. | |
| 2007/0014872 A1 | 1/2007 | Matheny et al. | |
| 2007/0014873 A1 | 1/2007 | Matheny | |
| 2007/0014874 A1 | 1/2007 | Matheny | |
| 2007/0248638 A1 | 10/2007 | Van Dyke et al. | |
| 2008/0065046 A1 | 3/2008 | Sabbah et al. | |
| 2008/0065048 A1 | 3/2008 | Sabbah et al. | |
| 2008/0260831 A1 | 10/2008 | Badylak et al. | |
| 2009/0012413 A1 | 1/2009 | Sabbah et al. | |
| 2010/0190741 A1 | 7/2010 | Cohen et al. | |
| 2011/0189140 A1 | 8/2011 | Christman et al. | |
| 2012/0156250 A1 | 6/2012 | Christman et al. | |
| 2013/0101563 A1 | 4/2013 | Matheny et al. | |
| 2013/0116198 A1 | 5/2013 | Matheny et al. | |
| 2013/0122108 A1 | 5/2013 | Matheny et al. | |
| 2013/0123176 A1 | 5/2013 | Matheny et al. | |
| 2013/0123348 A1 | 5/2013 | Matheny et al. | |
| 2013/0129831 A1 | 5/2013 | Matheny et al. | |
| 2013/0129833 A1 | 5/2013 | Matheny et al. | |
| 2013/0129834 A1 | 5/2013 | Matheny et al. | |
| 2013/0156862 A1 | 6/2013 | Badylak et al. | |
| 2018/0043057 A1 | 2/2018 | Kentner et al. | |

FOREIGN PATENT DOCUMENTS

| | | |
|---|---|---|
| WO | 2003/094697 A2 | 11/2003 |
| WO | 2003/094697 A3 | 5/2004 |
| WO | 2004/050013 A2 | 6/2004 |
| WO | 2004/098669 A1 | 11/2004 |
| WO | 2004/050013 A3 | 6/2005 |
| WO | 2006/021950 A1 | 3/2006 |
| WO | 2006/095342 A2 | 9/2006 |
| WO | 2008/109407 A2 | 9/2008 |
| WO | 2009/089110 A2 | 7/2009 |
| WO | 2010/039823 A2 | 4/2010 |
| WO | 2010/039823 A3 | 7/2010 |
| WO | 2017/008035 A1 | 1/2017 |
| WO | 2017/024193 A1 | 2/2017 |

OTHER PUBLICATIONS

DrugBank: Paclitaxel (DB01229). downloaded on Feb. 17, 2015 from www.drugbank.ca/drugs/DB01229. p. 1-17.

Badylak. The extracellular matrix as a scaffold for tissue reconstruction. seminars in CELL & Developmental Biology, vol. 13, 2002: pp. 377-383.

Rosso et al. From Cell-ECM Interactions to Tissue Engineering. Journal of Cellular Physiology 199:174-180 (2004).

Kornowski et al. Electromagnetic Guidance for Catheter-Based Transendocardial Injection: A :Platform for Intramyocardial Angiogenesis Therapy: Results in Normal and Ischemic Porcine Models. J Am Coll Cardiol 2000;35:1031-9.

(56) References Cited

OTHER PUBLICATIONS

PuraMatrix in vivo delivery protocol with and without cells. 3DM, Inc. downloaded from https://web.archive.org/web/20051224194005/ http://www.puramatrix.com/protocol_pdfs/PuraMatrix_InVivo.pdf. Dec. 24, 2005. p. 1-2 (Year: 2005).

BO PuraMatrix Peptide Hydrogel. BO Biosciences. 2004. p. 1-16 (Year: 2004).

Zhang et al. PuraMatrix: Self-assembling Peptide Nanofiber Scaffolds. A chapter in Scaffolding in Tissue Engineering. Downloaded from web.archive.org/web/20060321192812/http://www.3d-matrix.co.jp/dl_file/PuraMatrix_Introduction.pdf. 2006, p. 1-31. (Year: 2006).

Klein et al. Chapter 4. Injectable Collagen. Tissue Augmentation in Clinical Practice. edited by Arnold Klein.—2nd ed. p. 63-82 (Year : 2006).

Karmarkar et al. MR-Trackable Intramyocardial Injection Catheter, Magnetic Resonance in Medicine 51: 1163-1172 (Year: 2004).

Chinese Office Action mailed Nov. 5, 2018 for CN Application No. 201610675138.0 (15 pages with English translation).

Sheng et al., "Current Stem Cell Delivery Methods for Myocardial Repair," BioMed Research International, 2013, Article No. 547902, 15 pages.

Sherman et al., "Catheter-Based Delivery of Cells to the Heart," Nature Clinical Practice, Cardiovascular Medicine, 2006, 3(Supp. 1):S57-S64.

Badylak, et al., "Extracellular Matrix as a Biological Scaffold Material: Structure and Function," Acta Biomaterials 5, 2009, 1-13.

Wolf, et al., "A Hydrogel Derived from Decellularized Dermal Extracellular Matrix," Biomaterials, 2012, 33 (29):7028-38.

Non-Final Office Action mailed May 7, 2015 for U.S. Appl. No. 13/217,218 (8 pages).

European search report and search opinion dated Sep. 25, 2014 for EP Application No. 11820625.9.

Badylak, et al. Esophageal reconstruction with ECM and muscle tissue in a dog model. J Surg Res. Sep. 2005;128(1):87-97.

Badylak, et al. Naturally occurring extracellular matrix as a scaffold for musculoskeletal repair. Clin Orthop Relat Res. Oct. 1999;(367 Suppl):S333-43.

Badylak, et al. Resorbable bioscaffold for esophageal repair in a dog model. J Pediatr Surg. Jul. 2000;35(7):1097-103.

Badylak, et al. The use of extracellular matrix as an inductive scaffold for the partial replacement of functional myocardium. Cell Transplant. 2006;15 Suppl 1:S29-40.

Badylak, et al. The use of xenogeneic small intestinal submucosa as a biomaterial for Achilles tendon repair in a dog model. J Biomed Mater Res. Aug. 1995;29(8):977- 85.

Badylak. The extracellular matrix as a scaffold for tissue reconstruction. Semin Cell Dev Biol. Oct. 2002;13(5):377-83.

Badylak. Xenogeneic extracellular matrix as a scaffold for tissue reconstruction. Transpl Immunol. Apr. 2004;12(3-4):367-77.

Bernacca, et al. Polyurethane heart valve durability: effects of leaflet thickness and material. Int J Artif Organs. Jun. 1997;20(6):327-31.

Billiar, et al. Biaxial mechanical properties of the natural and glutaraldehyde treated aortic valve cusp—Part I: Experimental results. J Biomech Eng. Feb. 2000;122(1):23-30.

Brightman, et al. Time-lapse confocal reflection microscopy of collagen fibrillogenesis and extracellular matrix assembly in vitro. Biopolymers. Sep. 2000;54(3):222-34.

Chaudhuri, et al. Detection and gradation of oriented texture. Pattern Recogn Lett. 1993;14(2): 147-53.

Courtney, et al. Analysis and design of novel electrospun PEUU scaffolds for soft tissue engineering. The 8th Annual Meeting of the Tissue Engineering Society International, Oct. 22-25, 2005, Shanghai, P.R. China. Published on CD, Final Program and Abstract Book TESI 2005, Abstract# 193.

Courtney, et al. Analysis and design of novel electrospun PEUU scaffolds for soft tissue engineering. ASME 2005 Summer Bioengineering Conference, Vail, CO, Jun. 22-26, 2005. Published on CD, Proceedings of the 2005 Summer Bioengineering Conference Vail Cascade Resort and Spa, Vail, CO; Abstract# b0241329.

Courtney, et al. Analysis and design of novel electrospun PEUU scaffolds for soft tissue engineering. 2005 Annual Fall Mtg, Nov 28-Dec. 1, 2005, Boston, MA. Abstract L 13.1.

Courtney, et al. Design and analysis of tissue engineering scaffolds that mimic soft tissue mechanical anisotropy. Biomaterials. Jul. 2006;27(19):3631-8. Epub Mar. 2, 20060.

Courtney, et al. Incorporation of fiber tortuosity effects in a constitutive model for scaffolds. ASME 2006 Summer Bioengineering Conference, Jun. 21-25, 2006, Amelia Island, Florida. Published on CD, Proceedings of the 2006 Summer Bioengineering Conference, Abstract# BI02005-157686.

Courtney, et al. Meso- and micromechanics of elastomeric electrospun PEUU scaffolds for cardiovascular tissue engineering. Regenerate World Congress on Tissue Engineering and Regenerative Medicine, Apr. 25-27, 2006, Pittsburgh, PA. Published on CD, Conference Proceedings Regenerate World Congress on Tissue Engineering and Regenerative Medicine, Abstract # 572.

Courtney, et al. Micromechanics of electrospun poly ester urethane urea scaffolds for soft tissue engineering. Fifth World Congress of Biomechanics, July 29-Aug. 4, 2006, Munich, Germany. Published in Journal of Biomechanics 2006 39(Supp 1 ): S262.

Courtney, et al. Micromechanics of electrospun polyester urethane urea scaffolds. Society for Biomaterials 2006 Annual Meeting, Apr. 26-29, 2006, Pittsburgh, PA. Published on CD, Transactions of the 31st Annual Meeting of the Society for Biomaterials, vol. XXIX, Abstract# 163.

Courtney, et al. Structural and mechanical characterization of poly-(ester urethane) elastomeric scaffolds for cardiovascular soft tissue engineering. Society for Biomaterials 30th Annual Meeting, Memphis, TN, Apr. 27-30, 2005. Published on CD, Transactions of the 30th Annual Meeting.

De La Fuente, et al. Evaluation of porcine-derived small intestine submucosa as a biodegradable graft for gastrointestinal healing. J Gastrointest Surg. 96-1 01 (7) 2003.

Dedecker, et al. Small intestinal submucosa (SIS): prospects in urogenital surgery. Prog Urol. Jun. 2005; 15(3):405-10. (English-language Abstract included).

Deglau, et al. Surface modification of vascular tissue for targeted delivery of endothelial cells and microspheres. Abstract for Biomedical Engineering Society 2000 Annual Fall Meeting, Oct. 12-14, 2000. Ann Biomed Eng. 2000;28(Supplement):S-23.

Dejardin, et al. Tissue-engineered rotator cuff tendon using porcine small intestine submucosa. Histologic and mechanical evaluation in dogs. AJSM. 175-84 (29) 2001.

Duruisseau, et al. Endoscopic rehabilitation of vocal cord paralysis with a silicone elastomer suspension implant. Otolaryngol Head Neck Surg. Sep. 2004;131(3):241-7.

Freytes, et al. Biaxial strength of multilaminated extracellular matrix scaffolds. Biomaterials, 2004. 25(12): 2353-61.

Freytes, et al. Porcine Urinary Bladder Matrix Derived Gel for Tissue Engineering Applications. Regenerate World Congress and Society for Biomaterials: 2006. Pittsburgh, PA. (Poster and Abstract).

Frisk, et al. A concept for miniaturized 3-D cell culture using an extracellular matrix gel. Electrophoresis. Dec. 2005;26(24):4751-8.

Gelman, et al. Collagen fibril formation. Evidence for a multistep process. J Bioi Chem. Jan. 10, 1979;254(1): 180-6.

Gilbert, et al. Development of a Hybrid ECM/Porous Metal Scaffold for Connective Tissue Ingrowth. Regenerate World Congress Meeting: Apr. 2006. Pittsburgh, PA. (Poster and Abstract).

Grashow, et al. Biaixal stress-stretch behavior of the mitral valve anterior leaflet at physiologic strain rates. Ann Biomed Eng. Feb. 2006;34(2):315-25. Epub Feb. 1, 2006.

Guan, et al. Biodegradable poly( ether ester urethane)urea elastomers based on poly(ether ester) triblock copolymers and putrescine: synthesis, characterization and cytocompatibility. Biomaterials. Jan. 2004;25(1 ):85-96.

Guan, et al. Preparation and characterization of highly porous, biodegradable polyurethane scaffolds for soft tissue applications. Biomaterials. Jun. 2005;26(18):3961-71.

Guan, et al. Synthesis, characterization and cytocompatibility of polyurethaneurea elastomers with designed elastase sensitivity. Biomacromolecules. Sep.-Oct. 2005;6(5):2833-42.

(56) References Cited

OTHER PUBLICATIONS

Guan, et al. Synthesis, characterization, and cytocompatibility of elastomeric, biodegradable poly(ester-urethane)ureas based on poly(caprolactone) and putrescine. J Biomed Mater Res. Sep. 5, 2002;61 (3):493-503.
Hacking, et al. Fibrous tissue ingrowth and attachment to porous tantalum. J Biomed Mater Res, 631-8 (52) 2000.
Higuera, et al. Tendon reattachment to a metallic implant using an allogenic bone plate augmented with rhOP-1 vs. autogenous cancellous bone and marrow in a canine model. J Orthop Res. Sep. 2005;23(5):1 091-9. Epub Apr. 7, 2005.
Karlon, et al. Automated measurement of myofiber disarray in transgenic mice with ventricular expression of ras. Anat Rec. Dec. 1998;252(4):612-25.
Lee, et al. Nanofiber alignment and direction of mechanical strain affect the ECM production of human ACL fibroblast. Biomaterials. Apr. 2005;26(11 ):1261-70.
Lehman. Injectable and bulk-forming agents for enhancing the lower esophageal sphincter. Am J Med. Aug. 18, 2003;115 Suppl 3A:188S-91 S.
Lightner, et al. Injectable agents: present and future. Curr Urol Rep. Oct. 2002;3(5):408-13.
Matsuda, et al. Mechanoactive scaffold design of small-diameter artificial graft made of electrospun segmented polyurethane fabrics. J Biomed Mater Res A. Apr. 1, 2005 ;73(1):125-31.
Middleton, et al. Synthetic Biodegradable Polymers as Medical Devices. Medical Plastics and Biomaterials Magazine. Medical Plastics and Biomaterials Magazine. Mar. 1998, p. 30. Available at: http://devicelink.com/mpb/archive/98/03/002.htmI.
Nedovic, et al. Cell immobilization by electrostatic droplet generation. Landbauforsch Volk 2002, (241):11-17.
Office action dated Jan. 19, 2012 for U.S. Appl. No. 12/040,140.
Office action dated Jul. 22, 2013 for U.S. Appl. No. 13/684,830.
Office action dated Oct. 30, 2013 for U.S. Appl. No. 13/217,218.
Radisic, et al. Medium perfusion enables engineering of compact and contractile cardiac tissue. Am J Physiol Heart Circ Physiol. Feb. 2004;286(2):H507-16. Epub Oct. 9, 2003.
Ray, et al. Isolation of vascular smooth muscle cells from a single murine aorta. Methods Cell Sci. 2001 ;23(4):185-8.
Reddy, et al. A simplified method for the analysis of hydroxyproline in biological tissues. Clin Biochem. Jun. 1996;29(3):225-9.
Riboldi, et al. Electrospun degradable polyesterurethane membranes: potential scaffolds for skeletal muscle tissue engineering. Biomaterials. Aug. 2005;26(22):4606-15. Epub Jan. 7, 2005.
Rimsay, et al. Biochemical Analysis of Hyaline Gelation: An Essential Step in the Assembly of the Sea Urchin Extraembryonic Matrix, the Hyaline Layer. Archives of Biochemistry and Biophysics. 2003; (414): 279-286.
Ringel, et al. The application of tissue engineering procedures to repair the larynx. J Speech Lang Hear Res. Feb. 2006;49(1 ): 194-208.
Robinson, et al. Extracellular matrix scaffold for cardiac repair. Circulation. Aug. 30, 2005;112(9 Suppl):I135-43.
ROBINSON. Roles for Ca2+, Mg2+ and NaCI in modulating the self-association reaction of hyalin, a major protein component of the sea-urchin extraembryonic hyaline layer. Biochem J. Nov. 15, 1988;256(1 ):225-8.
Sacks. Biaxial mechanical evaluation of planar biological materials. J Elasticity 2000; 61(1-3):199-246.
Santucci, et al. Resorbable extracellular matrix grafts in urologic reconstruction. Int Braz J Urol. May-Jun. 2005;31 (3):192-203. Review. Erratum in: Int Braz J Urol. Jui.-Aug. 2005;31 (4):414.
Sarikaya, et al. Antimicrobial activity associated with extracellular matrices. Tissue Eng. Feb. 2002;8(1):63-71.
Stankus, et al. Fabrication of biodegradable elastomeric scaffolds with sub-micron morphologies. J Biomed Mater Res A. Sep. 15, 2004;70(4):603-14.
Stankus, et al. Fabrication of cell microintegrated blood vessel constructs through electrohydrodynamic atomization. Biomaterials. Jun. 2007;28(17):2738-46. Epub Feb. 20, 2007.
Stankus, et al. Microintegrating smooth muscle cells into a biodegradable, elastomeric fiber matrix. Biomaterials. Feb. 2006;27(5):735-44. Epub Aug. 10, 2005.
Suwiwat, et al. Expression of extracellular matrix components versican, chondroitin sulfate, tenascin, and hyaluronan, and their association with disease outcome in node-negative breast cancer. Clin Cancer Res. Apr. 1, 2004;10(7):2491-8.
Temple, et al. Electrostatic transportation of living cells through air. Abstracts of Papers, 223 ACS National Meeting, Orlando, FL, Apr. 7-11, 2002.
Veazey, et al. Mammalian cell delivery via aerosol deposition. J Biomed Mater Res B Appl Biomater. Feb. 15, 2005;72(2):334-8.
Venere, et al. New materials hold promise for human healing applications. Purdue News, Mar. 22, 2001.
Williams, et al. Collagen fibril formation. Optimal in vitro conditions and preliminary kinetic results. J Bioi Chem. Sep. 25, 1978;253(18):6578-85.
Wood, et al. Use of a particulate extracellular matrix bioscaffold for treatment of acquired urinary incontinence in dogs. JAm Vet Med Assoc. Apr. 1, 2005 ;226(7):1 095-7.
Wright Medical Technology. Comparative analysis: Graft Jacket™ Periosteum Replacement Scaffold & SIS™ Porcine Small Intestine Submucosa. Copyright in 2002.
Xu, et al. Aligned biodegradable nanofibrous structure: a potential scaffold for blood vessel engineering. Biomaterials. Feb. 2004;25(5):877-86.
Xu, et al. Injectable tissue-engineered cartilage with different chondrocyte sources. Plast Reconstr Surg. Apr. 15, 2004;113(5):1361-71.
Zantop, et al. Extracellular matrix scaffolds are repopulated, in part, by bone marrow-derived cells in a mouse model of achilles tendon reconstruction. J Orthop Res. Jun. 2006;24(6):1299-309.
Zhang, et al. Artificial matrix helps neonatal cardiomyocytes restore injured myocardium in rats. Artif Organs. Feb. 2006;30(2):86-93.
Badylak et al. "Extracellular Matrix for Myocardial Repair," The Heart Surgery Forum, 2003, 6(2):E20-E26.
Danielsen, "Mechanical Properties of Reconstituted Collagen Fibrils. I Influence of a Glycosaminoglycan: Dermatan Sulfate," Connective Tissue Research, 1982, 9(4):219-225.
Freytes et al., "Preparation and Rheological Characterization of a Gel Form of the Porcine Urinary Bladder Matrix," Biomaterials, 2008, 29:1630-1637.
International search report and written opinion dated Apr. 30, 2012 for PCT/US2011/049026.
Lungu, The Influence of Glycosaminoglycan Type on the Collagen-Glycosaminoglycan Porous Scaffolds, "Digest Journal of Nanomaterials and Biostructures," 2011, 6(4):1867-1875.
Madden et al., "Proangiogenic Scaffolds as Functional Templates for Cardiac Tissue Engineering," Proc Natl Acad Sci U S A., 2010, 107(34):15211-15216.
Obrink, "The Influence of Glycosaminoglycans on the Formation of Fibers from Monomeric Tropocollagen in vitro," Eur. J. Biochem., 1973, 34:129-137.
Office action dated Jan. 10, 2013 for U.S. Appl. No. 13/075,774.
Office action dated May 18, 2012 for U.S. Appl. No. 13/075,774.
Office action dated Dec. 19, 2012 for U.S. Appl. No. 13/217,218.
Qing et al., "Optimal Method for Rat Skeletal Muscle Decellularization," Division of Stem Cell and Tissue Engineering, 2009, 23(7):836-9. (English abstract only.).
Seif-Naraghi et al., "Design and Characterization of an Injectable Pericardial Matrix Gel: A Potentially Autologous Scaffold for Cardiac Tissue Engineering," Tissue Engineering: Part A, 2010, 16(6):2017-2027.
Singelyn, et al., "Naturally Derived Myocardial Matrix as an Injectable Scaffold for Cardiac Tissue Engineering," Biomaterials, 2009, 30(29):5409-5416.
Wainwright et al., "Preparation of Cardiac Extracellular Matrix from an Intact Porcine Heart," Tissue Engineering: Part C, 16(3):525-532.
Leor, 2005, "Cells, Scaffolds, and Molecules for Myocardial Tissue Engineering," Pharmacology & Therapeutics, vol. 105, pp. 151-163.

(56) References Cited

OTHER PUBLICATIONS

Stella, et al., "On the Biomechanical Function of Scaffolds for Engineering Load-Bearing Soft Tissues," Acta Biomaterialia, 2010, in press.
PCT International Search Report for PCT/US2009/059015 dated Apr. 19, 2010 (2 pages).
Jawad et al., 2008, "Myocardial Tissue Engineering," British Medical Bulletin, 83:31-47.
Ott et al., 2008, "Perfusion-Decellularized Matrix: Using Nature's Platform to Engineer a Bioartificial Heart," Medline, XP-002612650.
Supplementary European Search Report for EP Application No. 09 81 8438 mailed Jun. 12, 2012 (8 pages).

\* cited by examiner

COMPOSITIONS AND METHODS FOR TISSUE REPAIR WITH EXTRACELLULAR MATRICES

CROSS REFERENCES TO RELATED APPLICATIONS

This application is a continuation of U.S. application Ser. No. 13/891,562, filed May 10, 2013, which is a divisional of U.S. application Ser. No. 13/075,774, filed Mar. 30, 2011, which is a continuation of PCT Application No. PCT/US2009/059015, filed Sep. 30, 2009, and which claims priority benefit of U.S. Provisional Application No. 61/101,332 filed Sep. 30, 2008, each of which are incorporated herein by reference in their entireties.

STATEMENT OF GOVERNMENT INTEREST

This invention was made with government support under grant No. OD004309 awarded by National Institutes of Health (NIH). The government has certain rights in the invention.

BACKGROUND

Various publications, including patents, published applications, technical articles and scholarly articles are cited throughout the specification. Each of these cited publications is incorporated by reference herein, in its entirety.

Cardiovascular disease is the leading cause of death in the United States. The most common cause of cardiovascular disease is myocardial infarction (MI), which occurs when a coronary artery is occluded. MI results in the death of cardiomyocytes and extracellular matrix (ECM) degradation, followed by scar tissue deposition. Eventually heart failure is onset, and the heart dilates, leading to decreased pumping efficiency. As there are very few cardiac progenitors in the heart, and these progenitors do not divide readily and regeneration of the heart tissue does not occur naturally. Current treatments for heart failure rely heavily on invasive surgical procedures and do little to repair damaged heart tissue.

More recently investigated procedures utilize the injection of healthy cells into the left ventricle (LV) infarct wall in an attempt to regenerate the myocardium, although studies have shown poor injected cell survival. Cells including adult and embryonic stem cells, induced pluripotent stem cells, and differentiated cells such as cardiomyocytes have been typically cultured on surfaces or scaffolds coated with one, or a few extracellular matrix proteins. Yet, in vivo, these cells exist in a highly complex extracellular milieu.

Some naturally derived materials are currently being investigated for injection into the myocardium including fibrin, collagen, alginate, matrigel, and gelatin. None of these provide a significant amount of the native components of the heart extracellular matrix. For arrhythmia treatment, current non-ablative forms include injection of fibrin and cells. Existing matrices for in vitro cell culture for cardiomyocytes, stem cells, and other cardiac relevant cells include collagen, laminin, SURECOAT (CELLUTRON, mixture of collagen and laminin), and gelatin.

Current efforts to prevent heart failure after myocardial infarction have focused on cellular transplantation to replace necrotic cardiomyocytes, prevent negative left ventricular remodeling, and regenerate heart tissue. However, without the proper matrix, cardiomyocyte growth in vitro and survival in vivo have been poor. There is a need for improved compositions for cardiac repair, arrhythmia treatment, and cardiac cell culture. Similarly, there is also a need for improved compositions for skeletal muscle repair, regeneration and cell culturing.

SUMMARY OF THE INVENTION

In one aspect, the invention provides a composition comprising decellularized extracellular matrix derived from cardiac tissue. In some instances, the cardiac tissue is myocardial tissue and in other instances the tissue is pericardial tissue. The composition can be injectable. The composition can be formulated to be in liquid form at room temperature, typically 20° C. to 25° C., and in gel form at a temperature greater than room temperature or greater than 35° C.

In some instances, said cardiac tissue is selected from the group consisting of human hearts, primate hearts, porcine hearts, bovine hearts, or any other mammalian or animal hearts, including but not limited to, goat heart, mouse heart, rat heart, rabbit heart, and chicken heart.

In some instances, the composition is configured to be injected into the infarct wall following a myocardial infarction. In some instances, the composition is configured to be delivered to a tissue through a small gauge needle (e.g., 27 gauge or smaller). In some instances, said composition is suitable for implantation into a patient.

In some instances, the composition comprises naturally occurring chemotaxis, growth and stimulatory factors that recruit cells into the composition. In some instances the composition comprises native glycosaminioglycans. In some instances, the composition further comprises non-naturally occurring factors that recruit cells into the composition.

In some instances, the composition further comprises a population of exogenous therapeutic cells. The cells can be stem cells or other precursors of cardiomyocytes or other cardiac-related cells.

In some instances, the composition further comprises a therapeutic agent, and as such is configured as a drug delivery vehicle. In some instances, the composition is configured as a non-destructive conduction block to treat, for example, arrhythmias. In some instances, the composition is configured to coat surfaces, such as tissue culture plates or scaffolds, to culture cardiomyocytes or other cell types relevant to cardiac repair.

In one aspect, the invention provides a method of producing a composition comprising decellularized cardiac extracellular matrix comprising: obtaining a cardiac tissue sample having an extracellular matrix component and non-extracellular matrix component; processing the cardiac tissue sample to remove the non-extracellular matrix component to obtain decellularized cardiac extracellular matrix, including extracellular proteins and polysaccharides; and sterilizing the decellularized cardiac extracellular matrix. In some instances, said method further comprises the step of lyophilizing and grinding up the decellularized cardiac extracellular matrix. In some instances, said method further comprises the step of enzymatically treating, solubilizing or suspending the decellularized cardiac extracellular matrix. In some instances, said decellularized cardiac extracellular matrix is digested with pepsin at a low pH.

In some instances, said method further comprises the step of suspending and neutralizing said decellularized cardiac extracellular matrix in a solution. In some instances, said solution is a phosphate buffered solution (PBS) or saline solution which can be injected through a high gauge needle into the myocardium. In some instances, said composition is formed into a gel at body temperature. In some instances, said composition further comprises cells, drugs, proteins or other therapeutic agents that can be delivered within or attached to the composition before, during or after gelation.

In some instances, said solution is placed into tissue culture plates or wells, incubated at above 35° C. or about 37° C. to form into a gel that is used for cell culture. In one aspect, the invention provides a method of culturing cells on an adsorbed matrix comprising the steps of: providing a solution comprising decellularized extracellular matrix derived from cardiac tissue into a tissue culture device; incubating said tissue culture plates device; removing said solution; and culturing cells on the adsorbed matrix. In some instances, said cells are cardiomyocytes or other cell types relevant to cardiac repair.

In one aspect, the invention provides a therapeutic method for cardiac tissue repair in a subject comprising injecting or implanting a therapeutically effective amount of a composition comprising decellularized extracellular matrix derived from cardiac tissue into a subject in need thereof.

In another aspect, a composition herein comprises decellularized extracellular matrix derived from skeletal muscle tissue. The composition can be injectable. The composition can be liquid at room temperature and is in a gel form at temperatures greater than room temperature. In some instances, the composition is configured to be injected into the infarct wall following a myocardial infarction. In some instances, the composition is configured to be delivered to a tissue through a 27 g or smaller needle.

In some embodiments, the composition comprising decellularized extracellular matrix derived from skeletal muscle tissue herein retains native glycosaminoglycans. In some instances, the composition comprises naturally occurring factors that recruit cells into the composition. In some instances, the composition comprises non-naturally occurring factors that recruit cells into the composition. In some instances, said composition is configured to coat tissue culture surfaces or scaffolds to culture cells relevant to skeletal muscle repair.

In an aspect, a method of producing a composition is disclosed herein that comprises decellularized skeletal muscle extracellular matrix comprising: obtaining from a subject a skeletal muscle tissue sample having an extracellular matrix and non-extracellular matrix components; processing skeletal muscle tissue sample to remove the non-extracellular matrix component to obtain decellularized skeletal muscle extracellular matrix and extracellular proteins and polysaccharides; and sterilizing the decellularized skeletal muscle extracellular matrix. In some instances, said method further comprises the step of lyophilizing and grinding up the decellularized skeletal muscle extracellular matrix. In some instances, said method further comprises the step of enzymatically treating, solubilizing, or suspending the decellularized skeletal muscle extracellular matrix. In some instances, said decellularized skeletal muscle extracellular matrix is digested with pepsin at a low pH. In some instances, said method further comprises the step of suspending and neutralizing or altering the pH of said decellularized cardiac extracellular matrix in a solution. In some instances, said solution is a PBS, saline or other buffer solution configured to be injected through a small diameter needle into the myocardium. The solution can be formed into a gel at body temperature. The solution can further comprise cells, drugs, proteins, or polysaccharides that can be delivered inside, attached to the material before, during, or after gelation. In some instances, the solution is placed into tissue culture plates or wells, incubated at 37° C., or temperature above room temperature, to form into a gel that is used for cell culture.

In an aspect, a method of culturing cells on an adsorbed matrix comprises the steps of: providing a solution comprising decellularized extracellular matrix derived from skeletal muscle tissue into a tissue culture device; incubating said tissue culture plates device; removing said solution; and culturing cells on the adsorbed matrix. In some instances, said cells are skeletal myoblasts, stem cells or other cell types relevant to skeletal muscle repair.

In an aspect, a therapeutic method for skeletal muscle repair in a subject comprises implanting a composition comprising decellularized extracellular matrix derived from skeletal muscle tissue.

DETAILED DESCRIPTION OF THE INVENTION

Figure 1:
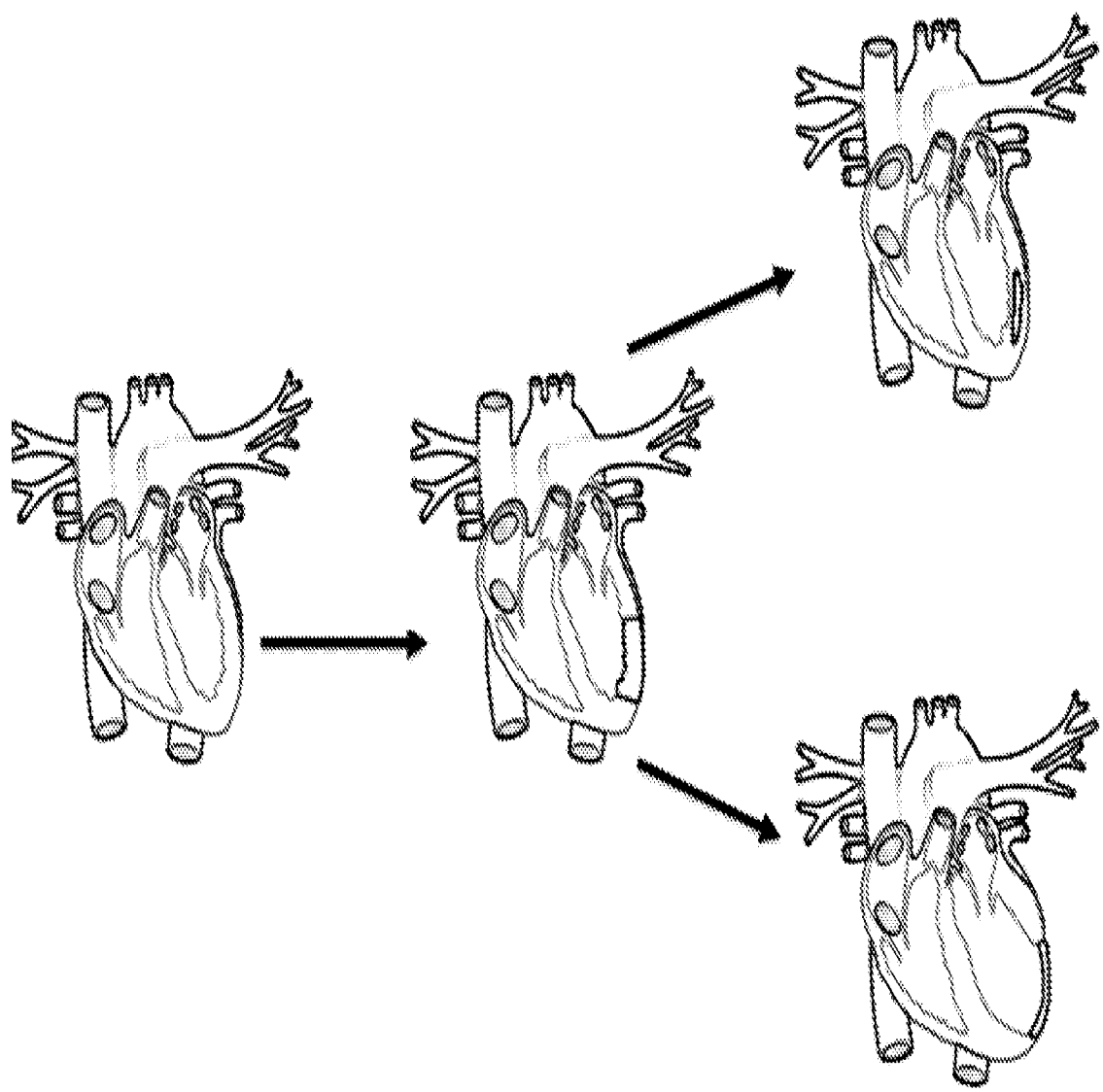
FIG. 1 illustrates an exemplary heart resulting from the method of delivering a composition of the present invention at top or a standard therapy at bottom.

In certain preferred embodiments, the present invention provides a decellularized cardiac extracellular matrix (ECM) composition which can be used, for example, to deliver therapeutic agents, including cells, into the heart wall following a myocardial infarction. The ECM of the present invention can be derived from the native or natural matrix of mammalian heart tissue. Described herein are compositions comprising cardiac ECM which can be used for injection into cardiac tissue in need of therapeutic treatment. The ECM can also be used to recruit cells into the injured tissue or as a drug delivery vehicle. The composition can also be used to support injured tissue or change the mechanical properties. Another use of the present invention is as a non-destructive conduction block to treat, for example, arrhythmias. In some instances, heart or cardiac ECM as described herein is derived from myocardial tissue. In other instances, heart or cardiac ECM as described herein is derived from pericardial tissue.

A composition comprising the decellularized cardiac ECM as described herein can help regenerate defective or absent myocardium and restore cardiac function. The ECM composition can be derived from an animal or synthetic source. An extracellular matrix composition herein can further comprise one or more additional components, for example without limitation: an exogenous cell, a peptide, polypeptide, or protein, a vector expressing a DNA of a bioactive molecule, and other therapeutic agents such as drugs, cellular growth factors, nutrients, antibiotics or other bioactive molecules. Therefore, in certain preferred embodiments, the ECM composition can further comprise an exogenous population of cells such as cardiomyocyte precursors, as described below.

In some instances, methods of delivery are described wherein the composition can be placed in contact with a defective, diseased or absent myocardium, resulting in myocardial tissue regeneration and restoration of contractility, conductivity, or healthy function to the heart muscle. In some instances, the composition herein can recruit endogenous cells within the recipient and can coordinate the function of the newly recruited or added cells, allowing for cell proliferation or migration within the composition.

Prior efforts to prevent heart failure after myocardial infarction (MI) have focused on cellular transplantation to replace necrotic cardiomyocytes, prevent negative left ventricular (LV) remodeling, and regenerate heart tissue. A variety of cell types have been explored as cellular transplantation therapies, including cardiomyocytes, skeletal myoblasts, mesenchymal and embryonic stem cells. Unfortunately, without the proper matrix, cellular survival in vivo has been poor. Some naturally derived matrices that have been used to attempt to aid in cell retention and survival upon injection in the prior art include fibrin, collagen, matrigel, alginate, and gelatin. However, none of these materials adequately mimics the native components found specifically in the cardiac extracellular matrix.

Current injectable scaffolds to treat the heart post-MI fail to provide all desired components of the extracellular matrix that cells require to thrive. Thus, cell survival in such scaffolds has been limited. In certain embodiments, this invention provides a native cardiac ECM decellularization and gelation method to create an in situ scaffold for cellular transplantation. An appropriate digestion and preparation protocol has been provided herein that can create nanofibrous gels. The gel solution is capable of being injected into the myocardium or infarct, thus demonstrating its potential as an in situ gelling scaffold. Since a decellularized cardiac ECM best mimics the natural cardiac environment, it improves cell survival and retention upon injection at the site of myocardial infarction, thus encouraging myocardial tissue regeneration.

FIG. 1 illustrates an exemplary method of delivering a composition herein. A healthy heart is shown on the left. After myocardial infarction shown in the central diagram, no current standard therapies, such as available pharmaceuticals and medical devices alone, effectively avoid the death of the cardiomyocytes, negative LV remodeling, LV dilation, and heart failure, as shown in the bottom right schematic. The present invention ameliorates this problem by delivering an injectable composition as described herein. Delivering a composition herein to a LV provides increased regeneration, reduced infarct size, reduced LV remodeling, and improved cardiac function, as shown in the upper right schematic diagram of the heart.

The invention features decellularized cardiac extracellular matrix, as well as methods for the production and use thereof. In particular, the invention relates to a biocompatible composition comprising decellularized cardiac extracellular matrix derived directly from cardiac tissue, and is used for treating defective, diseased, damaged or ischemic tissues or organs in a subject, preferably a human heart, by injecting or implanting the biocompatible composition comprising the decellularized cardiac extracellular matrix into the subject. Other embodiments of the invention concern decellularized skeletal muscle, extracellular matrix compositions, methods of use and methods of production In some instances, the decellularized cardiac extracellular matrix is derived from native cardiac tissue selected from the group consisting of human, porcine, bovine, goat, mouse, rat, rabbit, chicken or any other mammalian or animal hearts. In some embodiments, the biocompatible composition comprising the decellularized cardiac extracellular matrix is in an injectable gel or solution form, and can be used for cardiac repair by transplanting or delivering cells contained therein into the infarct wall following a myocardial infarction, or recruiting the patient's own cells into the injured cardiac tissue. In other instances, the biocompatible material comprising a decellularized cardiac ECM is, for example, a patch, an emulsion, a viscous liquid, fragments, particles, microbeads, or nanobeads.

In some instances, the invention provides biocompatible materials for culturing cardiomyocytes or other cardiac relevant cells in research laboratories, or in a clinical setting prior to transplantation and for cardiac repair. Methods for manufacturing and coating a surface, such as tissue culture plates or wells, with decellularized cardiac extracellular matrix are also provided. The biocompatible materials of the invention are also suitable for implantation into a patient, whether human or animal.

The invention further provides a method of producing a biocompatible material comprising the decellularized cardiac extracellular matrix of the invention. Such method comprises the steps of: (a) obtaining a cardiac tissue sample having an extracellular matrix component and non-extracellular matrix component; (b) processing the cardiac tissue sample to remove at least a portion or substantially all of the non-extracellular matrix component to obtain decellularized cardiac extracellular matrix; and (c) sterilizing the decellularized cardiac extracellular matrix. In certain embodiments, the cardiac tissue sample is isolated from a mammal such as a non-primate (e.g., cows, pigs, horses, cats, dogs, rats, etc.) or a primate (e.g., monkey and human), or an avian source (e.g., chicken, duck, etc.). Decellularization procedures for the cardiac tissue sample are performed using one or more physical, chemical and/or biological techniques, known in the art and as taught herein.

For human therapy, there are many potential sources for the cardiac extracellular matrix material: human heart (including autologous, allogeneic, or cadaveric), porcine heart, bovine heart, goat heart, mouse heart, rat heart, rabbit heart, chicken heart, and other animal sources. Unlike total heart transplantation, one donor heart can be used to treat many people. Non-human animals are a source of heart extracellular matrix without the need for human donors. As a research reagent, non-human animal sources can be utilized.

In certain embodiments, the method of processing the cardiac extracellular matrix is as follows. The heart tissue is first decellularized, leaving only the extracellular matrix. Decellularization can be performed with a perfusion of sodium dodecyl sulfate and phosphate buffered solution, for example. The heart extracellular matrix is then lyophilized, ground up, and digested with pepsin at a low pH, between about pH 1-6 or pH 1-4, or other matrix degrading enzymes such as matrix metalloproteinases.

To produce a gel form of the cardiac extracellular matrix for in vivo therapy, the solution comprising the heart extracellular matrix is then neutralized and brought up to the desired temperature, concentration and viscosity using PBS/saline. In certain embodiments, the ECM concentration can be 1-20 mg/mL, or 2-8 mg/mL. The solution comprising the heart extracellular matrix can then be injected through a high gauge needle, such as 27 gauge or higher, into the myocardium. At body temperature, e.g., 36.8° C.±0.7° C., such solution then forms into a gel. Cells, drugs, proteins, or other therapeutic agents can also be delivered inside the cardiac ECM gel.

To produce a gel form of the cardiac extracellular matrix for in vitro uses, the solution comprising the heart extracellular matrix is neutralized and brought up to the desired concentration using PBS/saline. In certain embodiments, the ECM concentration can be 1-20 mg/mL, or 2-8 mg/mL. Such solution can then be placed onto any solid surface such as into tissue culture plates/wells. Once placed in an incubator at 37° C. or above room temperature, the solution forms a gel that can be used for cell culture.

The invention also provides a therapeutic method for cardiac repair in a subject comprising injecting or implanting in part or in its entirety the biocompatible cardiac ECM material of the invention into a patient. The invention further provides a therapeutic method for treating arrhythmia or other defective, diseased, damaged or ischemic tissue or organ in a subject comprising injecting or implanting the biocompatible material of the invention in situ.

The compositions herein can comprise a decellularized ECM derived from cardiac tissue and another component or components. In some instances, the amount of ECM in the total composition is greater than 90% or 95% or 99% of the composition by weight. In some embodiments, the ECM in the total composition is greater than 1%, 5%, 10%, 20%, 30%, 40%, 50%, 60%, 70%, or 80% of the composition by weight.

Decellularized extracellular matrices are prepared such that much of the bioactivity for myocardial tissue regeneration is preserved. Exemplary bioactivity of the compositions herein include without limitation: control or initiation of cell adhesion, cell migration, cell differentiation, cell maturation, cell organization, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, chemotaxis, and MMP or other enzyme activity.

The compositions comprise an extracellular matrix that is substantially decellularized. In some instances, a decellularized matrix comprises no living native cells with which the ECM naturally occurs. In some instances, a substantially decellularized matrix comprises less than 1%, 2%, 3%, 4%, 5%, 6%, 7%, 8%, 9% or 10% native cells by weight.

As described herein, a composition can comprise a decellularized cardiac ECM and different tissue decellularized EMC or a synthetic or naturally occurring polymer. Exemplary polymers herein include, but are not limited to: polyethylene terephthalate fiber (DACRON), polytetrafluoroethylene (PTFE), glutaraldehyde-cross linked pericardium, polylactate (PLA), polyglycol (PGA), hyaluronic acid (HA), polyethylene glycol (PEG), polyethelene, nitinol, and collagen from animal and non-animal sources (such as plants or synthetic collagens). In some instances, a polymer of the composition is biocompatible and biodegradable and/or bioabsorbable. Exemplary biodegradable or bioabsorbable polymers include, but are not limited to: polylactides, polyglycolides, polycarprolactone, polydioxane and their random and block copolymers. A biodegradable and/or bioabsorbable polymer can contain a monomer selected from the group consisting of a glycolide, lactide, dioxanone, caprolactone, trimethylene carbonate, ethylene glycol and lysine.

The polymer material can be a random copolymer, block copolymer or blend of monomers, homopolymers, copolymers, and/or heteropolymers that contain these monomers.

The biodegradable and/or bioabsorbable polymers can contain bioabsorbable and biodegradable linear aliphatic polyesters such as polyglycolide (PGA) and its random copolymer poly(glycolide-co-lactide-) (PGA-co-PLA). Other examples of suitable biocompatible polymers are polyhydroxyalkyl methacrylates including ethylmethacrylate, and hydrogels such as polyvinylpyrrolidone and polyacrylamides. Other suitable bioabsorbable materials are biopolymers which include collagen, gelatin, alginic acid, chitin, chitosan, fibrin, hyaluronic acid, dextran, polyamino acids, polylysine and copolymers of these materials. Any combination, copolymer, polymer or blend thereof of the above examples is contemplated for use according to the present invention. Such bioabsorbable materials may be prepared by known methods.

Therefore, methods are described herein for preparing a composition comprising decellularized ECM derived from cardiac muscle tissue. The invention also provides ECM compositions and methods derived from skeletal muscle tissue in an analogous process. Related compositions, devices and methods of production and use also are provided.

In certain embodiments, the viscosity of the composition increases when warmed above room temperature including physiological temperatures approaching about 37° C. According to one non-limiting embodiment, the ECM-derived composition is an injectable solution at room temperature and other temperatures below 35° C. In another non-limiting embodiment the gel can be injected body temperature above about 37° C. or near body temperature, but gels more rapidly at increasing temperatures. A gels forms after approximately 15-20 minutes at physiological temperature of 37° C. A general set of principles for preparing an ECM-derived gel is provided along with preferred specific protocols for preparing gels in the following Examples which are applicable and adaptable to numerous tissues including without limitation heart and skeletal muscle.

The compositions which may include cells or other therapeutic agents may be implanted into a patient, human or animal, by a number of methods. In some instances, the compositions are injected as a liquid into a desired site in the patient.

Commercially available ECM preparations can also be combined in the methods, devices and compositions described herein. In one embodiment, the ECM is derived from small intestinal submucosa (SIS). Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton, Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.).

In some instances, the solution, gel form, and adsorbed form of the heart extracellular matrix of the invention provide all the constituents at the similar ratios found in vivo. For arrhythmia treatment, the extracellular matrix of the invention can be delivered which can allow for cardiac tissue regeneration after resolution of the arrhythmia. For in vitro cell culture for cardiomyocytes and other cardiac relevant cells, the gel and adsorbed forms of the heart extracellular matrix of the invention contain all or many of the same extracellular matrix cues that the cells recognize in vivo as compared to the commonly used collagen, laminin, SURECOAT (CELLUTRON, mixture of collagen and laminin), and gelatin.

The compositions herein provide a gel or solution form of heart extracellular matrix, and the use of these forms of heart extracellular matrix for cardiac repair, arrhythmia treatment, and cell culture for example. In one embodiment, the heart tissue is first decellularized, leaving only the extracellular matrix. The matrix is then lyophilized, ground or pulverized into a fine powder, and solubilized with pepsin or other enzymes, such as, but not limited to, matrix metalloproteases, collagenases, and trypsin.

For gel therapy, the solution is then neutralized and brought up to the appropriate concentration using PBS/saline. In one embodiment, the solution can then be injected through a needle into the myocardium (either via cathether, through the ribs, or during an open chest procedure. The needle size can be without limitation 22 g, 23 g, 24 g, 25 g, 26 g, 27 g, 28 g, 29 g, 30 g, or smaller. In one embodiment, the needle size through which the solution is injected is 27 g. Delivery can also occur through a balloon infusion catheter or other non-needle cathether. Dosage amounts and frequency can routinely be determined based on the varying condition of the injured tissue and patient profile. At body temperature, the solution can then form into a gel. In yet another embodiment, gel can be crosslinked with glutaraldehye, formaldehyde, bis-NHS molecules, or other crosslinkers.

In yet another embodiment, the ECM can be combined with other therapeutic agents, such as cells, peptides, proteins, DNA, drugs, nutrients, antibiotics, survival promoting additives, proteoglycans, and/or glycosaminolycans. In yet another embodiment, the ECM can be combined and/or crosslinked with a synthetic polymer. Examples of synthetic polymers include, but are not limited to: polyethylene terephthalate fiber (DACRON™), polytetrafluoroethylene (PTFE), polylactic acid (PLA), polyglycolic acid (PGA), polyethylene glycol (PEG), polyethylene glycol diacrylate (P'EGDA), polyethylene, polystyrene and nitinol.

In yet another embodiment, ECM solution or gel can be injected into the infarct area, border zone, or myocardium alone or in combination with above-described components for endogenous cell ingrowth, angiogenesis, and regeneration. In yet another embodiment, the composition can also be used alone or in combination with above-described components as a matrix to change mechanical properties of the heart and/or prevent negative left ventricular remodeling. In yet another embodiment, the composition can be delivered with cells alone or in combination with the above-described components for regenerating myocardium. In yet another embodiment, the composition can be used alone or in combination with above-described components for creating a conduction block to treat arrhythmias.

In one embodiment for making a soluble reagent, the solution is brought up in a low pH solution including but not limited to 0.5 M, 0.1, or 0.01 M acetic acid or 0.1M HCl to the desired concentration and then placed into tissue culture plates/wells, coverslips, scaffolding or other surfaces for tissue culture. After placing in an incubator at 37° C. for 1 hour, or overnight at room temperature, the excess solution is removed. After the surfaces are rinsed with PBS, cells can be cultured on the adsorbed matrix. The solution can be combined in advance with peptides, proteins, DNA, drugs, nutrients, survival promoting additives, proteoglycans, and/or glycosaminoglycans before, during, or after injection/implantation.

The present invention provides enhanced cell attachment and survival on both the therapeutic composition and adsorbed cell culturing composition forms of the heart extracellular matrix in vitro. The soluble cell culturing reagent form of the heart extracellular matrix induces faster spreading, faster maturation, and/or improved survival for cardiomyocytes compared to standard plate coatings.

Previous studies have shown that is difficult to use human embryonic stem cell (hESC) derived cardiomyocytes for treatment of myocardial infarction. In some instances, efficient differentiation and in vivo yield of mature ventricular cardiomyocytes has hampered the effectiveness of treatment. Previously, modulation of differentiation has been largely addressed in vitro, for example, with addition of soluble factors to cell culture media. This process has been limited by difficulty in differentiating beyond a fetal phenotype.

In addition to soluble factors, extracellular matrix can also play a large role in cell differentiation. Some matrices comprising chemical cues have been investigated for adult cells, including adult progenitors, however limited work has been performed on ECM effects on ESCs, particularly for hESCs. In many instances, hESC derived cardiomyocytes are delivered in a pro-survival mixture consisting of soluble factors and matrigel.

In an embodiment herein, a biomimetic matrix derived from native cardiac tissue is disclosed. In some instances, a matrix resembles the in vivo cardiac environment in that it contains many or all of the native chemical cues found in natural cardiac ECM. In some instances, through crosslinking or addition or other materials, the mechanical properties of healthy adult or embryonic myocardium can also be mimicked. As described herein, cardiac ECM can be isolated and processed into a gel using a simple and economical process, which is amenable to scale-up for clinical translation.

In some instances, a composition as provided herein can comprise a matrix and exogenously added or recruited cells. The cells can be any variety of cells. In some instances, the cells are a variety of cardiac or cardiovascular cells including, but not limited to: stem cells, progenitors, cardiomyocytes, vascular cells, and fibroblasts derived from autologous or allogeneic sources.

The invention thus provides a use of a gel made from native decellularized cardiac extracellular matrix to support isolated neonatal cardiomyocytes or stem cell progenitor derived cardiomyocytes in vitro and act as an in situ gelling scaffold, providing a natural matrix to improve cell retention and survival in the left ventricle wall. A scaffold created from cardiac ECM is well-suited for cell transplantation in the myocardium, since it more closely approximates the in vivo environment compared to currently available materials.

A composition herein comprising cardiac ECM and exogenously added cells can be prepared by culturing the cells in the ECM. In addition, where proteins such as growth factors are added into the extracellular matrix, the proteins may be added into the composition, or the protein molecules may be covalently or non-covalently linked to a molecule in the matrix. The covalent linking of protein to matrix molecules can be accomplished by standard covalent protein linking procedures known in the art. The protein may be covalently or linked to one or more matrix molecules.

In one embodiment, when delivering a composition that comprises the decellularized cardiac ECM and exogenous cells, the cells can be from cell sources for treating the myocardium that include allogenic, xenogenic, or autogenic sources. Accordingly, embryonic stem cells, fetal or adult derived stem cells, induced pluripotent stem cells, cardiomyocyte progenitors, fetal and neonatal cardiomyocytes, myofibroblasts, myoblasts, mesenchymal cells, parenchymal cells, epithelial cells, endothelial cells, mesothelial cells, fibroblasts, hematopoetic stem cells, bone marrow-derived progenitor cells, skeletal cells, macrophages, adipocytes, and autotransplanted expanded cardiomyocytes can be delivered by a composition herein. In some instances, cells herein can be cultured ex vivo and in the culture dish environment differentiate either directly to heart muscle cells, or to bone marrow cells that can become heart muscle cells. The cultured cells are then transplanted into the mammal, either with the composition or in contact with the scaffold and other components.

Adult stem cells are yet another species of cell that can be part of a composition herein. Adult stem cells are thought to work by generating other stem cells (for example those appropriate to myocardium) in a new site, or they differentiate directly to a cardiomyocyte in vivo. They may also differentiate into other lineages after introduction to organs, such as the heart. The adult mammal provides sources for adult stem cells in circulating endothelial precursor cells, bone marrow-derived cells, adipose tissue, or cells from a specific organ. It is known that mononuclear cells isolated from bone marrow aspirate differentiate into endothelial cells in vitro and are detected in newly formed blood vessels after intramuscular injection. Thus, use of cells from bone marrow aspirate can yield endothelial cells in vivo as a component of the composition. Other cells which can be employed with the invention are the mesenchymal stem cells administered with activating cytokines. Subpopulations of mesenchymal cells have been shown to differentiate toward myogenic cell lines when exposed to cytokines in vitro.

Human embryonic stem cell derived cardiomyocytes can be grown on a composition herein comprising a cardiac matrix. In some instances, hESC-derived cardiomyocytes grown in the presence of a composition herein provide a more in vivo-like morphology. In some instances, hESC-derived cardiomyocytes grown in the presence of a composition herein provide increased markers of maturation.

The invention is also directed to a drug delivery system comprising decellularized cardiac extracellular matrix for delivering cells, drugs, molecules, or proteins into a subject for treating defective, diseased, damaged or ischemic tissues or organs. In one embodiment, the inventive biocompatible material comprising the decellularized cardiac extracellular matrix alone or in combination with other components is used as a non-destructive conduction block for treatment of arrhythmias. Therefore, the inventive biocompatible material can be used to transplant cells, or injected alone to recruit native cells or other cytokines endogenous therapeutic agents, or act as a exogenous therapeutic agent delivery vehicle.

The composition of the invention can further comprise cells, drugs, proteins, or other biological material such as, but not limited to, erythropoietin (EPO), stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (EGGS), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), matrix metalloproteinase (MMP), tissue inhibitor matrix metalloproteinase (TIMP), interferon, interleukins, cytokines, integrin, collagen, elastin, fibrillins, fibronectin, laminin, glycosaminoglycans, hemonectin, thrombospondin, heparan sulfate, dermantan, chondrotin sulfate (CS), hyaluronic acid (HA), vitronectin, proteoglycans, transferrin, cytotactin, tenascin, and lymphokines.

Tissue culture plates can be coated with either a soluble ligand or gel form of the extracellular matrix of the invention, or an adsorbed form of the extracellular matrix of the invention, to culture cardiomyocytes or other cell types relevant to cardiac repair. This can be used as a research reagent for growing these cells or as a clinical reagent for culturing the cells prior to implantation. The extracellular matrix reagent can be combined with other tissue matrices and cells.

For gel reagent compositions, the solution is then neutralized and brought up to the appropriate concentration using PBS/saline or other buffer, and then be placed into tissue culture plates and/or wells. Once placed in an incubator at 37° C., the solution forms a gel that can be used for any 2D or 3D culture substrate for cell culture. In one embodiment, the gel composition can be crosslinked with glutaraldehye, formaldehyde, bis-NHS molecules, or other crosslinkers, or be combined with cells, peptides, proteins, DNA, drugs, nutrients, survival promoting additives, proteoglycans, and/or glycosaminolycans, or combined and/or crosslinked with a synthetic polymer for further use.

The invention further provides an exemplary method of culturing cells adsorbed on a decellularized cardiac extracellular matrix comprising the steps of: (a) providing a solution comprising the biocompatible material of decellularized ECM in low pH solution, including but not limited to, 0.5 M, or 0.01 M acetic acid or 0.1M HCl to a desired concentration, (b) placing said solution into tissue culture plates or wells, (c) incubating said tissue culture plates or wells above room temperature such as at 37° C., for between 1 hour and overnight (or at room temperature to 40° C.), (d) removing excess solution, (e) rinsing said tissue culture plates or wells with PBS, and (f) culturing cells on the adsorbed matrix. Cells that can be cultured on the adsorbed matrix comprising the cardiac extracellular matrix of the invention include cardiomyocytes or other cell types relevant to cardiac repair, including stem cells and cardiac progenitors.

In some instances a composition comprises crosslinkers including, but not limited to, common collagen crosslinkers, hyaluronic acid crosslinkers, or other protein cross-linkers with altered degradation and mechanical properties.

In an instance, a method of making the composition herein comprises electrospinning. In some instances, a method herein is configured to control the nanofiber size, shape, or thickness.

In some instances, contractility can be induced into the composition, for example, with cells or external pacing. Contractility can create cyclic stress to promote a more natural myocardium.

In some instances, cell influx and angiogenesis can be induced into the composition, for example, when the composition comprises linked groups or embedded factors, such as angiogenic factors.

In some instances, a composition herein may contain microbeads. Microbeads can be a part of the composition or delivered by the composition. Exemplary microbeads can be any variety of materials, for example, natural or synthetic. In some instances, the microbeads can have varied degradation properties or comprise, for example, MMP inhibitors, growth factors, or small molecules.

In some instances, the composition can comprise a biological group that can act as an adhesive or anchor where the composition is delivered.

In an instance, a composition can be a bioadhesive, for example, for wound repair. In some instances, a composition herein can be configured as a cell adherent. For example, the composition herein can be coating or mixed with on a medical device or a biologic that does or does not comprises cells. For example, the composition herein can be a coating for a synthetic polymer vascular graft. In some instances, the composition includes an anti-bacterial or anti-bacterial agents could be included.

Methods herein can comprise delivering the composition as a wound repair device. For example, after cardiac ablation, the composition can be delivered to improve healing.

In an instance, a composition comprises an alginate bead that is coated with an ECM composition as described herein.

In some instances, the composition is injectable. An injectable composition can be, without limitation, a powder, liquid, particles, fragments, gel, or emulsion. The injectable composition can be injected into a heart or in many instances, injected into the left ventricle, right ventricle, left atria, right atria, or valves of a heart. The compositions herein can recruit, for example without limitation, endothelial, smooth muscle, cardiac progenitors, myofibroblasts, stem cells, and cardiomyocytes.

Methods of making the compositions herein can include decellularizing tissue from any age animal or human by methods well known in the art.

In some instances, a composition herein comprises ECM and a natural or synthetic polymer. For example, a composition herein comprises a natural polymer such as collagen, chitosan, alginate, glycosaminoglycans, fibrin, or hyaluronic acid. In another example, a composition herein comprises a synthetic polymer, for example without limitation, polyethylene glycol, poly(glycolic)acid, poly(lactic acid), poly(hydroxy acids), polydioxanone, polycaprolactone, poly(ortho esters), poly(anhydrides), polyphosphazenes, poly(amino acids), pseudo-poly(amino acids), conductive polymers (such as polyacetylene, polypyrrole, polyaniline), or polyurethane or their potential copolymers. In some instances, a composition here comprise ECM and both a natural and a synthetic polymer. A composition herein can be a multi-material by linking an ECM and another polymer material, for example, via reaction with amines, free thiols, or short peptides that can self assemble with the ECM.

Methods herein include delivery of a composition comprising an ECM. Exemplary methods include, but are not limited to: direct injection during surgery; direct injection through chest wall; delivery through catheter into the myocardium through the endocardium; delivery through coronary vessels; and delivery through infusion balloon catheter. The composition can also be delivered in a solid formulation, such as a graft or patch or associated with a cellular scaffold. Dosages and frequency will vary depending upon the needs of the patient and judgment of the physician.

In some instances, a composition herein is a coating. The coating can comprise an ECM from any tissue for example cardiac muscle, skeletal muscle, pericardium, liver, adipose tissue, and brain. A coating can be used for tissue culture applications, both research and clinical. The coating can be used to coat, for example without limitation, synthetic or other biologic scaffolds/materials, or implants. In some instances, a coating is texturized or patterned. In some instances, a method of making a coating includes adsorption or chemical linking. A thin gel or adsorbed coating can be formed using an ECM solution form of the composition. In some instances, a composition herein is configured to seal holes in the heart such as septal defects.

A composition herein can also be developed from other tissues, such as skeletal muscle, pericardium, liver, adipose tissue, and brain. The compositions may be used as coating for biologics, medical devices or drug delivery devices.

The reconstruction of skeletal muscle, which is lost by injury, tumor resection, or various myopathies, is limited by the lack of functional substitutes. Surgical treatments, such as muscle transplantation and transposition techniques, have had some success; however, there still exists a need for alternative therapies. Tissue engineering approaches offer potential new solutions; however, current options offer incomplete regeneration. Many naturally derived as well as synthetic materials have been explored as scaffolds for skeletal tissue engineering, but none offer a complex mimic of the native skeletal extracellular matrix, which possesses important cues for cell survival, differentiation, and migration.

The extracellular matrix consists of a complex tissue-specific network of proteins and polysaccharides, which help regulate cell growth, survival and differentiation. Despite the complex nature of native ECM, in vitro cell studies traditionally assess cell behavior on single ECM component coatings, thus posing limitations on translating findings from in vitro cell studies to the in vivo setting. Typically, purified matrix proteins from various animal sources are adsorbed to cell culture substrates to provide a protein substrate for cell attachment and to modify cellular behavior. However, these approaches would not provide an accurate representation of the complexity microenvironment. More complex coatings have been used, such as a combination of single proteins, and while these combinatorial signals have shown to affect cell behavior, it is not as complete as in vivo. For a more natural matrix, cell-derived matrices have been used. Matrigel is a complex system; however, it is derived from mouse sarcoma, and does not mimic any natural tissue. While many components of ECM are similar, each tissue or organ has a unique composition, and a tissue specific naturally derived source may prove to be a better mimic of the cell microenvironment.

Skeletal muscles are composed of bundles of highly oriented and dense muscle fibers, each a multinucleated cell derived from myoblasts. The muscle fibers in native skeletal muscle are closely packed together in an extracellular three-dimensional matrix to form an organized tissue with high cell density and cellular orientation to generate longitudinal contraction. Skeletal muscle can develop scar tissue after injury which leads to a loss of functionality. The engineering of muscle tissue in vitro holds promise for the treatment of skeletal muscle defects as an alternative to host muscle transfer. Tissue engineering compositions must be biocompatible and capable of being vascularised and innervated.

The extracellular matrix (ECM) consists of a complex tissue-specific network of proteins and polysaccharides, which help regulate cell growth, survival and differentiation. Despite the complex nature of muscle ECM, in vitro cell studies traditionally assess muscle cell behavior on single ECM component coatings, thus posing limitations on translating findings from in vitro cell studies to the in vivo setting. Overcoming this limitation is important for cell-mediated therapies, which rely on cultured and expanded cells retaining native cell behavior over time.

In an aspect, a composition herein comprises ECM that is derived from porcine skeletal and cardiac muscle. The composition can be developed for substrate coating for a variety of applications. In some instances, the ECM of the composition retains a complex mixture of muscle-specific ECM components after solubilization. In some instances, the coatings herein can more appropriately emulate the native muscle ECM in vitro.

Skeletal myoblasts plated on skeletal muscle matrix displayed a significant increase in i) the number of myosin heavy chain positive myotubes, ii) the number of nuclei per myotube and iii) myotube width when compared to cells plated on traditional collagen type I coated substrates. Human embryonic stem cell (HES2) derived cardiac myocytes plated on myocardial matrix also displayed a significant increase in i) myofibrillar area, ii) number of cardiomyocyte nuclei per myofibrillar area and iii) desmosomal plaque size, which highlights larger more mature intercalated disc localization of the desmosomal cell-cell junction protein, desmoplakin, when compared to cells plated on traditional gelatin coated substrates. In some instances, the compositions are configured to provide the ability to reconstitute the in vivo muscle ECM. The composition may provide a tool to assess and maintain muscle and stem cell behavior in vitro similar to the native state, and may provide a tool for cell-mediated therapies in vivo.

Figure 2:
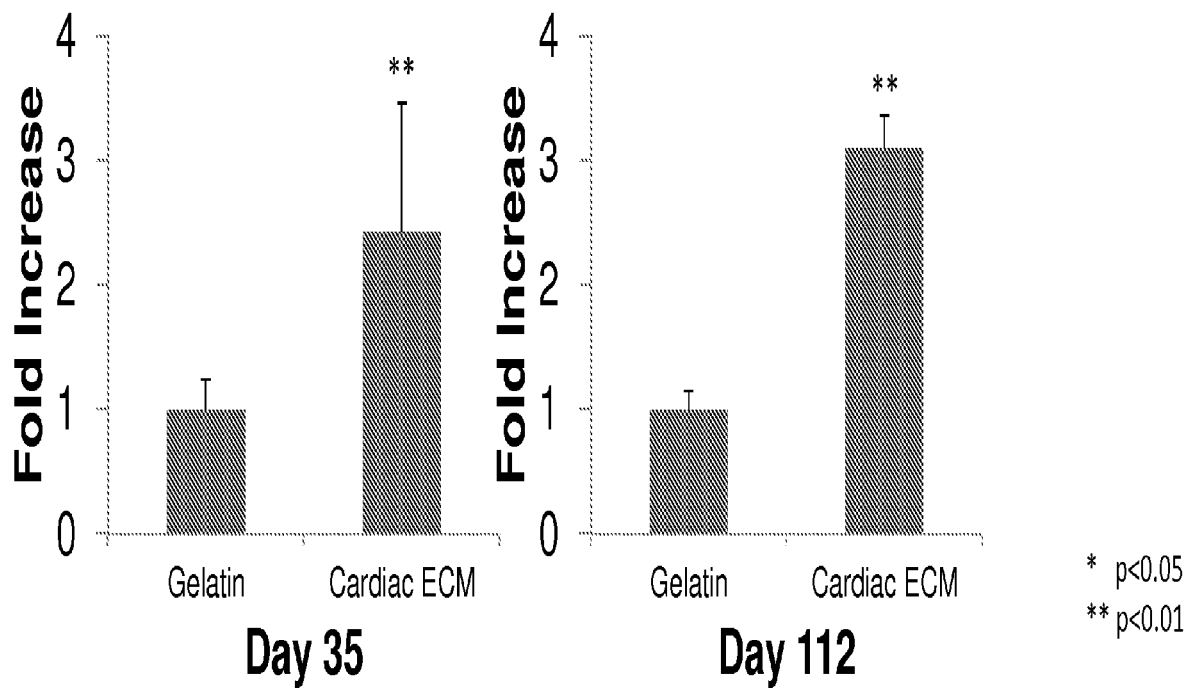
FIG. 2 illustrates the average myofibrillar area of human embryonic stem cell derived cardiomyocytes grown on cardiac ECM.
Figure 3:
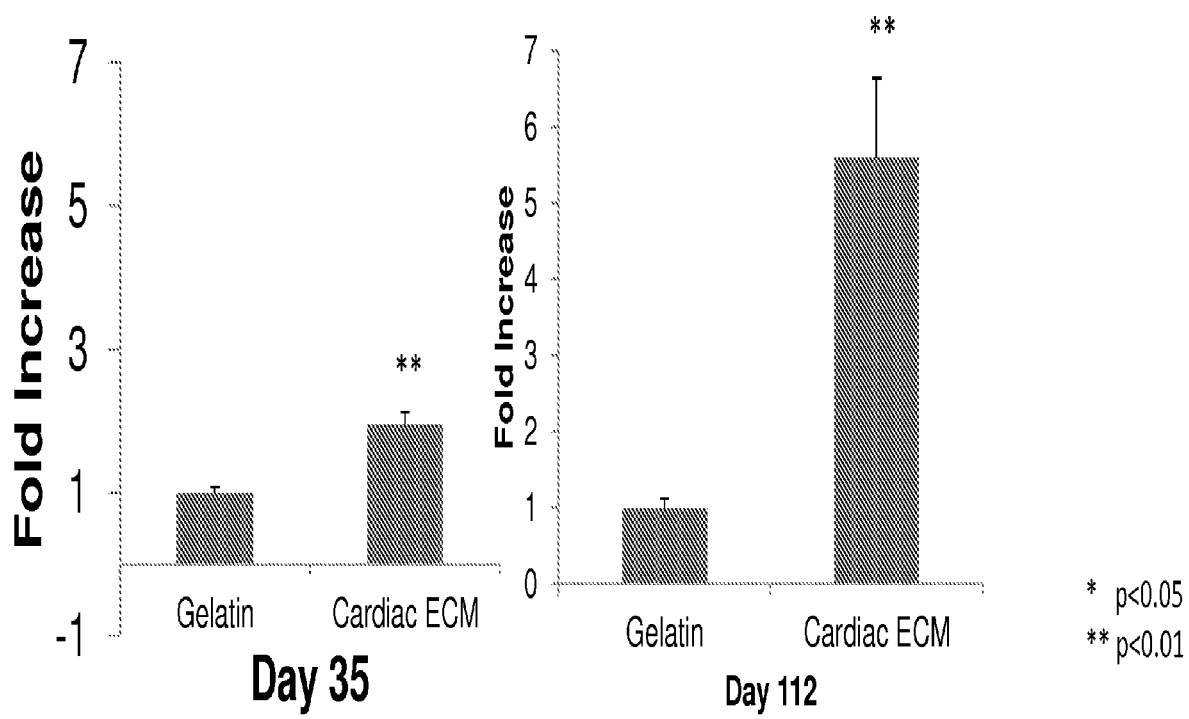
FIG. 3 illustrates the average number of human embryonic stem cell derived cardiomyocyte nuclei per myofibrillar area grown on cardiac ECM.
Figure 4:
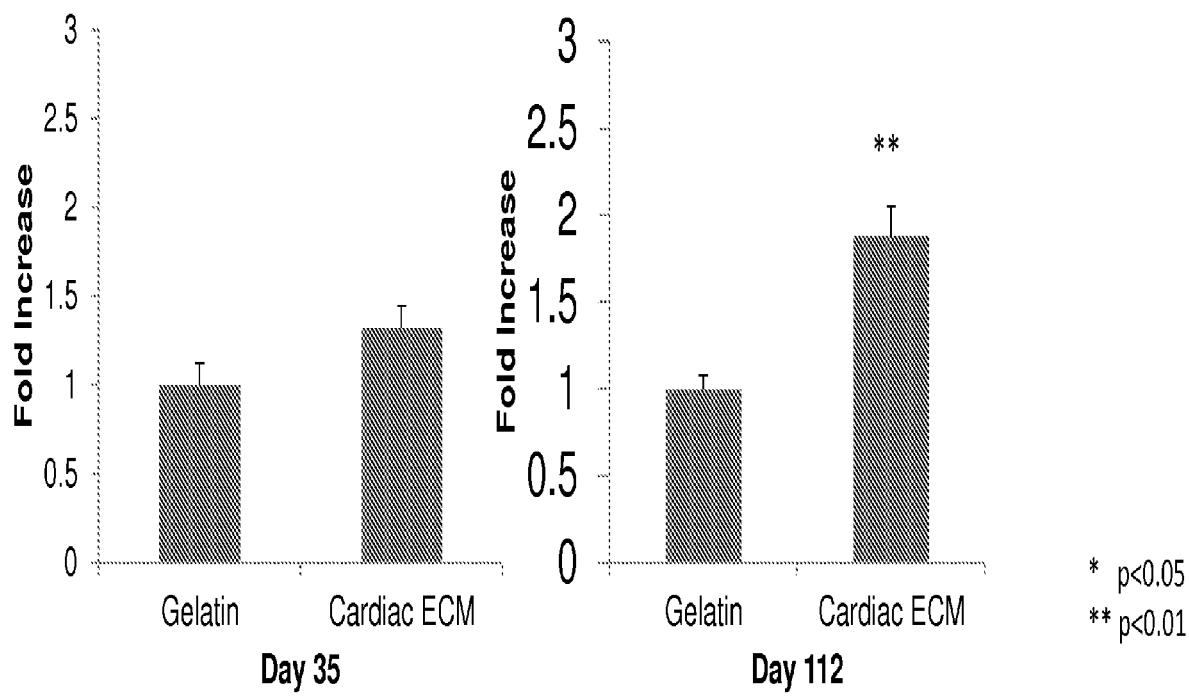
FIG. 4 shows average desmosome plaque size on cardiac ECM.

FIG. 2 illustrates the average myofibrillar area of cardiomyocytes was significantly greater when grown on cardiac ECM when compared to the standard coating of gelatin. FIG. 3 illustrates the average number of cardiomyocytes was significantly higher on cardiac ECM when compared to the standard coating of gelatin. As illustrated in FIG. 4, desmoplakin, an intracellular junction protein, specifically localized between cardiomyocytes and formed organized desmosomes at day 112 on cardiac ECM, but not on gelatin.

Figure 5:
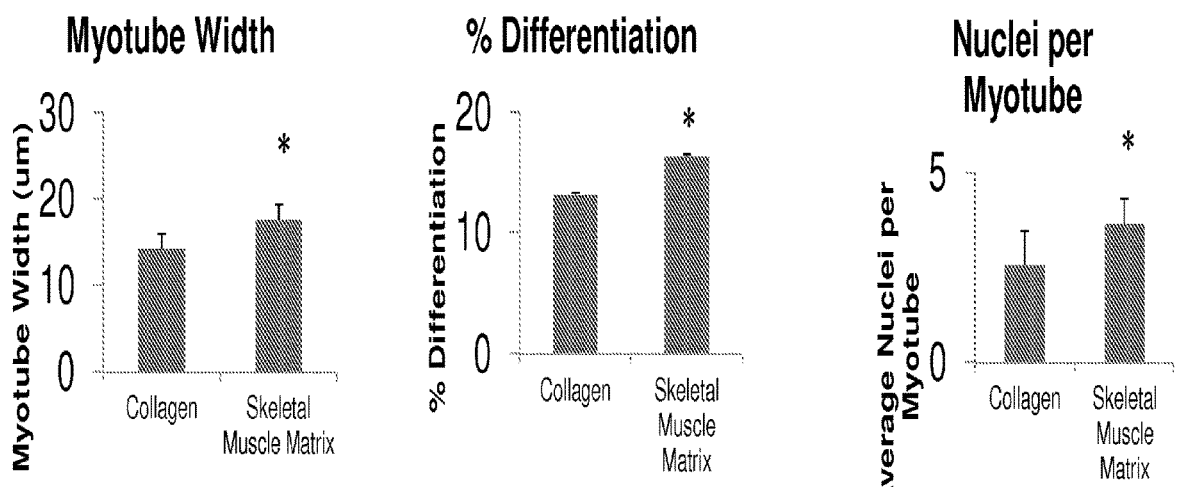
FIG. 5 illustrates skeletal myoblasts cultured on skeletal muscle matrix.
Figure 6:
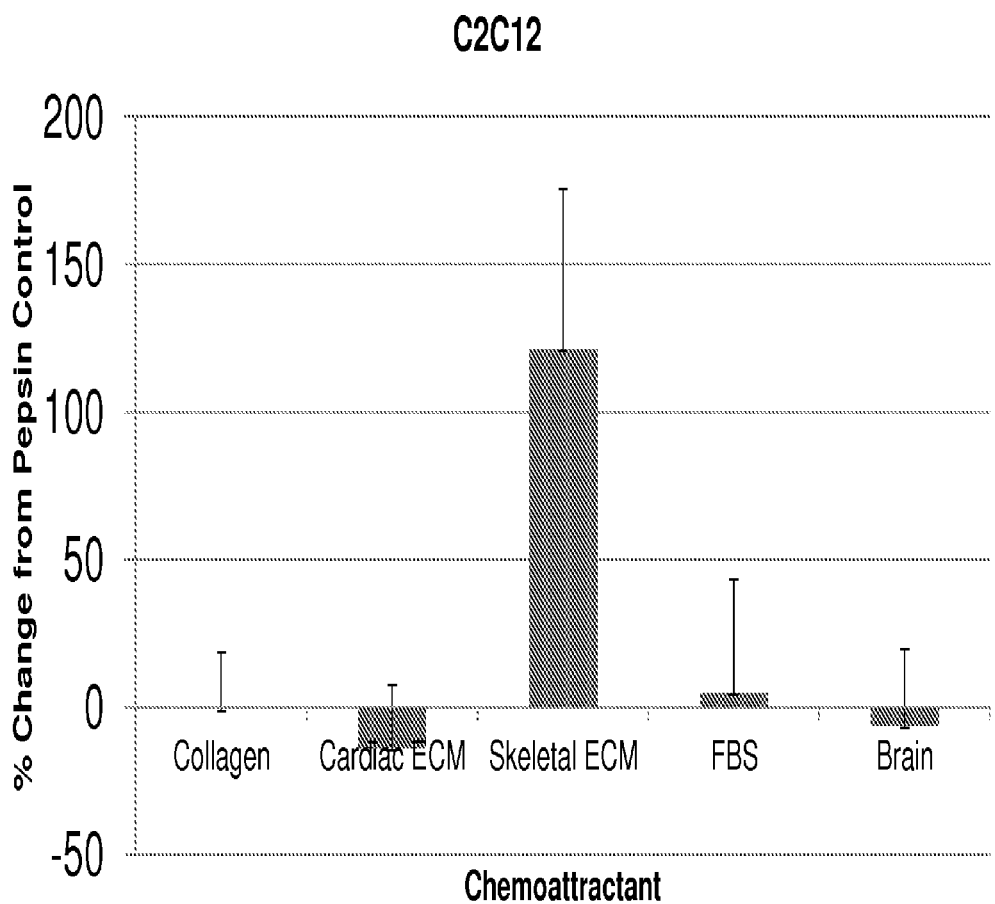
FIG. 6 illustrates that skeletal myoblasts migrate specifically towards skeletal muscle matrix.

As described herein a skeletal muscle matrix can be created in the same or a similar manner to the cardiac ECM. The skeletal muscle matrix can be injected into skeletal muscle for skeletal muscle tissue engineering. FIG. 5 illustrates skeletal myoblasts cultured on skeletal muscle matrix as described herein that demonstrated increased myotube size, increased differentiation, and had more nuclei per myotube than myoblasts cultured on collagen. Using a transwell migration assay, in vitro, skeletal myoblasts migrate specifically towards skeletal muscle matrix as illustrated in FIG. 6.

The invention is further illustrated by the following examples, which are not to be construed in any way as imposing limitations upon the scope thereof. It is apparent for skilled artisans that various modifications and changes are possible and are contemplated within the scope of the current invention.

Example 1

Various studies to treat MI have investigated the injection of cells directly into the infarct wall, although many studies have shown poor survival rates. The objective of this study is to examine the use of a gel as a growth platform for cell adhesion, growth, maturation, and delivery in vivo. It is provided that a gel composed of native heart extracellular matrix tissue can aid in cardiac tissue regeneration by promoting cell survival.

Female Sprague Dawley rats were enthanized and their hearts decellularized using a procedure modified from Ott et al. (Nature Medicine, 14(2), 213, 2008). Decellularized hearts were then lyophilized, rehydrated, pulverized, and lyophilized again to form a dry powder. The ECM was then minimally digested in pepsin and neutralized, as modified from Freytes et al. (Biomaterials 29: 1630, 2008).

More specifically, adult female Sprague Dawley rats were heparinized and anesthetized intraperitoneally with pentobarbital. The aorta and pulmonary artery were transected and the heart was removed. The aorta was cannulized and attached to a modified Langendorff setup.

The heart was decellularized using a modified, previously published technique. Briefly, the coronary vessels of the heart were retrogradedly perfused with a 1% sodium dodecyl sulfate (SDS) and PBS solution for 24 hours and then a 1% triton PBS solution for 30 minutes. Once the decellularization was complete, the heart was rinsed with deionized water and freeze dried in a lyophilizer.

Frozen hearts were rehydrated with water and then immersed in liquid nitrogen. Once frozen, hearts were systematically crushed within a ball and cup apparatus at 70 psi for 10 seconds. Pulverized heart particulates were then freeze dried. Once dry, lyophilized heart tissue was combined with 1% pepsin and amalgamated with 0.01M HCl to a concentration of 10 mg/mL. Solution was stirred at room temperature for 48 hours to allow for solubilization of the extracellular matrix tissue. After 48 hours, the HCl solution was aliquoted into Eppendorf tubes on ice and neutralized with 0.1N NaOH to pH 7.4.

Through the methods described above, a native rat cardiac ECM gel has been formed. Successful gelation of 2.5-8 mg/mL gels occurred within 15 minutes, as confirmed by the increased viscous nature of the material. Increased stiffness was observed with higher density gels.

The neutralized solution was diluted to concentration with 1×PBS, plated on a 96 well plate at 50 µL per well, and then transferred to an incubator at 37° C. and 5% CO2. After the gel had formed, 100 µL of isolated $2d$ neonatal cardiomyocyte cells were pipetted on top of the gel at 60,000 cells per well. After a few days, cells were examined for adherence to the gels.

After heart extracellular matrix tissue had been decellularized, pulverized and digested, a gel formed once the solution had been brought up to physiological conditions (pH=7.4, 37° C.). Gels formed with higher concentrations of ECM tissue in solution were stiffer and more opaque than gels formed with weaker concentrations of ECM. Cells plated on the gels were able to adhere to and survive on the gels.

Plating cardiomyocytes on the cardiac ECM gels at $1\times10^4$ showed successful adhesion and survival of cells to the ECM. The cells were cultured on the ECM for up to four days.

One hundred mL of cardiac ECM solution (7 mg/mL) was injected through a 30G needle into the LV free wall of an anesthetized rat. The present study shows that native heart extracellular matrix can be isolated, solubilized, and self-assembled into a gel when brought to physiological pH and temperature. Since the gel contains all of the native extracellular matrix components, albeit scrambled, it is provided that this matrix allows for successful adhesion and growth of cardiomyocytes in vitro and also once injected in vivo. Furthermore, a gel composed of the matrix derived originally from the heart ventricles is believed to support cardiomyocyte growth more successfully rather than other matrices such as collagen or fibrin gels since it more closely mimics the in vivo cardiac environment.

An injectable gel can potentially conform to any three-dimensional shape and improve cell transplant survival within the heart. Injected cardiomyocytes or cell which can differentiate into cardiomyocytes can aid in the regeneration of heart tissue, improve cardiac output. The method developed to create a native cardiac ECM gel platform with varied concentration and stiffness also provides an in vitro platform for cell growth and as an in situ engineered scaffold for generation. The native ECM provides the appropriate complex environment when injected in vivo to increase cell retention and promote tissue regeneration for myocardial tissue engineering.

Example 2

Cardiomyocytes have been typically cultured on surfaces coated with one, or possibly a few extracellular matrix (ECM) proteins. Yet, in vivo, cardiomyocytes exist in a highly complex extracellular milieu; an ECM that more closely mimics this native environment may be beneficial for cultured cardiomyocyte survival. Here, the use of native cardiac ECM that has been solubilized as a coating for cell culture of neonatal cardiomyocytes is reported.

Hearts were removed from Sprague-Dawley rats and decellularized using a modified Langendorff setup (modified from Ott et al., 2008). The decellularized hearts were lyophilized, rehydrated, and pulverized after freezing in liquid N2. The ECM was minimally digested in pepsin in 0.01M HCl. After 48 hours, 0.01 M acetic acid was added to make the final concentration of 1 mg/ml.

Cardiac myocytes were harvested from freshly dissected ventricles of 1 to 2 day old Sprague-Dawley rats using an isolation kit (Cellutron, Highland Park, NJ). The initial supernatant was discarded, but the subsequent 20 min digestions were strained and suspended in DMEM supplemented with 17% M199, 10% horse serum, 5% fetal bovine serum, and 1% penicillin/streptomycin. After isolation, the supernatant was pre-plated onto tissue culture polystyrene dishes to increase purity of cardiomyocytes through selective adhesion of fibroblasts.

Either 1 mg/ml native cardiac ECM or Collagen I (Sigma, St. Louis, MO) was adsorbed onto glass coverslips for one hour at 37° C. Isolated neonatal cardiomyocytes were plated at a density of 200,000/cm$^2$ and media was changed to low serum maintenance after 24 hours (DMEM, 18.5% M199, 5% HS, 1% FBS and antibiotics). Cell cultures were maintained at 37° C. and 5% CO2, monitored daily, and fresh maintenance media was exchanged every 2-3 days.

Cardiomyocytes adhered to the adsorbed native ECM, and formed a partially confluent layer. Initially, the cardiomyocytes adhered at a similar density to the collagen coating.

Both cell cultures began to spontaneously beat on Day 3 after plating. Cardiomyocytes cultured on collagen began to detach on Day 12, and stopped beating at Day 14. However, the cardiomyocytes cultured on the native heart ECM formed clearly defined fibrils, which beat at the same rate up until Day 28.

This study demonstrated that the use of native heart ECM for culture of cardiomyocytes is useful as it more closely mimics the conditions in vivo. The study also provides that neonatal cardiomyocytes adhere and continue to function longer on the native cardiac ECM than on the typical collagen coating. This new surface coating is beneficial for the culture of stem cell derived cardiomyocytes as well as cardiac progenitors.

Example 3

Here, cell coating use has been investigated for native heart extracellular matrix of adult ventricles that have been decellularized and solubilized. The advantages being that native heart ECM may have more components than traditional cell coatings, and be more readily available for use than pretreatment with other cell types.

Hearts were removed from Sprague-Dawley rats, and decellularized using a modified Langendorff setup (modified from Ott et al, 2008). The decellularized hearts were lyophilized, rehydrated, and pulverized after freezing in liquid nitrogen. The ECM was then digested in pepsin in 0.1M HCl. After 48 hours of digestion, 0.01 M acetic acid was added to dilute to the final concentration of 1 mg/ml.

Pepsin digestion of the native heart ECM was run in vertical gel electrophoresis in reducing conditions using DTT and compared against laminin (BD Biosciences), and calf skin collagen (Sigma). Gels were stained with Imperial Protein Stain (Pierce). Native heart ECM can demonstrate a more complex mixture of ECM components when compared to collagen and laminin.

Cardiac myocytes were harvested from the ventricles of 1 to 2 day old Sprague-Dawley rats using an isolation kit (Cellutron, Highland Park, NJ). The initial supernatant was discarded, but the subsequent 20 min digestions were strained and suspended in DMEM supplemented with 17% M199, 10% horse serum, 5% fetal bovine serum, and 1% penicillin/streptomycin. After isolation, the supernatant was pre-plated onto tissue culture polystyrene dishes to increase purity of cardiomyocytes through selective adhesion of fibroblasts.

Either 1 mg/ml native cardiac ECM or Collagen I (Sigma, St. Louis, MO) was adsorbed onto tissue culture 48-well plates for 1 hour at 37° C. Isolated neonatal cardiomyocytes were plated at a density of 200,000/cm2 and media was changed to low serum maintenance media after 24 hours (DMEM, 18.5% M199, 5% HS, 1% FBS and 1% penicillin/streptomycin). Cell cultures were maintained at 37° C. and 5% carbon dioxide, monitored daily, and fresh media was added every 2-3 days. Cultures were fixed at day 2, day 4, and day 7 and stained for alpha actinin, connexin43, pan-cadherin, actin and nuclei. Cardiomyocytes began to spontaneously beat in culture at Day 2. Cells cultured on collagen began detaching from the plate at Day 8. One set of cells cultured on native heart ECM continued beating until Day 45. All cells cultured on collagen stopped beating at Day 14.

Current cell culture coatings are generally simple proteins adsorbed onto tissue culture plates or scaffolds. Using a more complex environment is beneficial for cell survival and maturation. The native cardiac ECM was shown by this study to contain more complex components when compared to other standard cell culture coatings. Neonatal rat cardiomyocytes attached to native heart ECM as a coating for cell culture, and spontaneously began beating. Cardiomyocytes cultured on native cardiac ECM demonstrated increased actinin, connexin43, and pan-cadherin staining over time. Also, the neonatal cardiomyocytes had increased survivability and attachment on the native heart ECM when compared to collagen.

Example 4

Here, the use of a gel as described herein is investigated wherein the gel is made from native decellularized heart ECM. The gel may act as an in situ gelling scaffold, providing a natural cardiac matrix to improve cell retention and survival in the LV wall.

Female Sprague Dawley rats hearts and porcine hearts have been decellularized. Cardiac tissue was sliced to be ~2 mm thick and was rinsed with deionized water, then stirred in 1% sodium dodecyl sulfate (SDS) until decellularized, 4-5 days. An additional stir step in 1% Triton X-100 for 30 minutes ensured complete decellularization and was followed by overnight stirring in deionized water and a final rinse in deionized water.

Decellularized hearts were then lyophilized, pulverized or milled, and lyophilized again to form a dry powder. The ECM was then digested in pepsin and neutralized.

Solubilized cardiac ECM was then brought to physiologic or pH 8, through the addition of sodium hydroxide and 10×PBS. Neutralized cardiac extracellular matrix solution was then diluted with PBS to the desired concentration and allowed to gel in 96 well plates at 37° C. Successful gelation of 2.5-8 mg/mL gels was confirmed by visual inspection of the material. Increased stiffness was observed with higher concentration gels.

Various experimental conditions were tested to determine different digestion for gelation of cardiac ECM scaffolds. Vertical gel electrophoresis was performed to compare the content of digestion conditions, and to compare ECM content to rat tail collagen. Initial pH was determined to play an important role in digestion and gelation of cardiac ECM. Digestions were performed for 48-72 hours.

Gel electrophoresis reveals an incomplete digestion of native cardiac ECM by 0.01M HCl. Digestions of cardiac ECM in 0.1M HCl showed increased degradation. Thus, stronger acidic conditions were shown to improve digestion and gelation of cardiac ECM solutions. Comparison of the cardiac ECM to rat tail collagen demonstrates the presence of various additional peptides in the cardiac ECM.

Scanning electron microscopy was used to visualize the structure of the cardiac extracellular matrix gel form. Gels were fixed with 2.5% gluteraldehyde for 2 hours, followed by a series of ethanol rinses (30-100%), and critically point dried. Samples were sputter coated with chromium prior to imaging.

Solubilized native ECM at a concentration of 6 mg/mL cardiac ECM was successfully injected through a 30G needle into rat LV free wall, creating an in situ gelled scaffold, to which cardiomyocytes adhere and proliferate.

Example 5

In vitro chemoattractive properties of the cardiac decellularized ECM solution were tested using a commercially available migration assay kit. Briefly, human coronary artery endothelial cells (HCAECs) and rat aortic smooth muscle cells (RASMCs) were serum starved and migration was evaluated towards the matrix, collagen, pepsin, and fetal bovine serum. RASMCs show significant migration towards the matrix, while HCAECs show a trend. Thus, biochemical cues of the matrix have chemoattractive properties that could promote cell infiltration in vivo.

In vivo, arteriole formation was quantified within the injected region to assess neovascular formation. Arteriole density was significantly greater at 11 days post injection, as compared to 4 hours post injection.

Example 6

Several cell types have been shown to preserve cardiac function when injected into the myocardial wall following an MI. However, an acellular treatment could eliminate the complications of poor cell survival and the immune response, common with cell therapies.

Myocardial infarction was induced in rats using a 25 min ischemia-reperfusion model, via occlusion of the left anterior descending artery. At one week post-MI baseline function was calculated from MRI images.

Porcine myocardial ECM was decellularized in small pieces, in 1% SDS for several days, followed by a DI rinse overnight, lyophilization and milling to create a powder. Digestion was performed in 0.1 M HCl with pepsin to create a solubilized form of the material.

Solubilized ECM was brought to pH 7.4 using 1 M NaOH and diluted with PBS to be 6 mg/mL prior to injection. After MI surgery, animals were randomized into two groups and ECM or saline was injected into the LV free wall of female Sprague dawley rats through a 30 G needle, two weeks after infarction surgery.

4 weeks after injection surgery (6 weeks post-MI), cardiac function was again assessed using MRI.

Animals injected with ECM showed preserved function (as evaluated based on ejection fraction) at 6 weeks, while saline injected animals did not maintain cardiac function. End diastolic and end systolic volume were also preserved in ECM injected animals.

Example 7

Currently, stem cells and other cell types are in clinical trials for treatment of heart failure by delivery through a 27 G catheter into the myocardial wall. Porcine ventricular tissue was decellularized using SDS detergents, and processed to form a solubilized form of the matrix, and neutralized to physiologic pH and diluted to 6 mg/mL for injection.

Two Yorkshire pigs received a coil-induced myocardial infarction and were injected with myocardial matrix alone or with cells at two months post infarction.

Derived from fetal cardiac explants were pre-labeled with DiI, a cyotoplasmic stain, for histological identification. A pro-survival cocktail, shown to enhance hESC survival in a rodent model, was used.

Matrix alone or with cells was injected at a clinically relevant rate of 0.2 mL per 30 seconds through a catheter, as guided by NOGA mapping. 5 injections of 0.1 mL each were made of matrix alone or with cells into border zone regions of the infarct.

Matrix alone and matrix with cells was able to be successfully injected into the porcine heart, minimally invasively, without clogging the thin catheter.

Example 8

Here, the investigation and use of a gel derived from decellularized pericardial tissue is described as pertaining to its potential as an autologous therapy to improve cell retention and survival in the LV wall by promoting neovascularization in vivo.

Both porcine and human pericardia have been decellularized. Juvenile male farm pigs were euthanized and their pericardia were decellularized via procedures modified from Ott et al. (Nature Medicine, 14(2), 213, 2008). Specifically, pericardia were rinsed briefly in DI water, stirred in 1% sodium dodecyl sulfate (SDS) for 24 hours, then stirred in DI water for approximately 5 hours. Human pericardial tissue samples were collected from patients undergoing cardiothoracic surgeries. These samples were decellularized in a similar manner: a brief DI rinse, followed by 3 days in 1% SDS, followed by an overnight DI rinse. In both cases, complete decellularization was verified with histological staining.

The following is valid for both human and porcine pericardial ECM samples.

Decellularized pericardia, or pericardial ECM, were then frozen, lyophilized, and milled to form a fine, dry powder. The ECM powder was then digested with pepsin dissolved in HCl and neutralized, via methods modified from Freytes et al. (Biomaterials 29: 1630, 2008).

Gel electrophoresis (SDS-PAGE) indicated greater complexity than in pepsin-digested collagen, showing a wide range of smaller bands in the pericardium samples.

This complexity was confirmed by analyzing the samples with mass spectroscopy to identify protein fragments. Fragments of ECM proteins identified included collagen, elastin, fibrin, and a variety of proteoglycans.

When 150 ul of the neutralized solution was loaded into a 96-well plate and allowed to stand in an incubator, gelation was observed after 2-3 hours.

In vivo gelation was observed by injecting 60 ul of the neutralized ECM solution into the left ventricular (LV) wall of male Sprague Dawley rats. Histological staining of hearts sectioned from animals sacrificed 45 minutes after injection showed an area of gelled ECM visible in the LV wall.

In the same experiment, animals were maintained for two weeks, after which they were sacrificed and their hearts were harvested for sectioning. The ECM injection was still visible at this time point, but had been infiltrated by cells.

Immunohistochemistry was performed on tissue slices in order to identify the smooth muscle cells and endothelial cells, indicative of blood vessels. The presence of a large number of vessels within the ECM injection area indicates that the material promotes neovascularization.

Example 9

Surface coatings for in vitro cell culture have been typically made of one or a few extracellular matrix proteins. While this provides a cell adhesive surface, it does not mimic the in vivo extracellular microenvironment. Herein was developed a method to generate adsorbed coatings derived from extracellular matrices of various tissues, including cardiac, skeletal muscle, liver, pericardium, adipose tissue, and brain.

Tissue from porcine and rat origin was taken and decellularized. Cardiac tissue, skeletal muscle, and liver of both rat and porcine origin and brain, fat and pericardium of porcine origin was decellularized using various detergents. Cardiac, skeletal muscle, and liver tissue was sliced to be ~2 mm thick and was rinsed with deionized water, then stirred in 1% sodium dodecyl sulfate (SDS) in PBS until decellularized. The time it took to decellularize depended on tissue type. Brains were cut in half and stirred slowly in 0.001% SDS in PBS. Pericardial tissue was decellularized in 1% SBS in PBS, and adipose tissue was decellularized in 2.5 mM sodium deoxycholate, and then further processed with lipase. Other decellularization agents have also been tested. Decellularized tissue was then rinsed in deionized water to ensure removal of detergents, and then lyophilized.

The decellularized ECM was milled to form a dry powder, with the exception of decellularized brain and adipose ECM. The ECM was then digested to form a solubilized form used as a coating using pepsin in low acid conditions and then diluted using 0.1M acetic acid to bring it to the desired concentration of 1 mg/ml. Vertical Polyacrylamide Gel Electrophoresis was used and demonstrated a complex mixture of peptide fragments in each tissue type, which varied from tissue to tissue. This demonstrates that there exists tissue specific components in the decellularized ECM.

These coatings can be applied to surfaces in the same manner as typical single protein coatings. By culturing cells on tissue specific coatings that mimic the in vivo extracellular matrix microenvironment, there was better control of survival and cell morphology, and enhance differentiation.

Rat cortical neurons were cultured on brain matrix and compared to a standard coating of poly-l-lysine. Rat cortical neurons survived and retained their branched morphology longer on a brain matrix coating compared to the standard coating. Also observed was increased percent differentiation and increased myotube width when skeletal myoblasts were cultured on a skeletal muscle matrix coating compared to the standard coating of collagen. Finally, human embryonic stem cell derived cardiomyocytes displayed increased organization and maturation, including the formation cell-cell junctions when plated on a cardiac matrix coating compared to the typical gelatin coating.

These studies indicate the importance of using extracellular matrix mimics for cell culture, with implications towards many in vitro cell studies, including the promotion of stem cell maturation and differentiation.

Example 10

Here, the use of the gel is described herein is investigated wherein the gel is made from native decellularized skeletal muscle ECM. The gel can act as an in situ gelling scaffold, providing a natural skeletal muscle matrix to improve tissue regeneration in a leg injury model. The advantage is that the skeletal muscle ECM has components similar to the matrix found in vivo, and may provide a suitable platform for tissue engineering and regeneration, cell recruitment, and cell delivery.

Porcine skeletal muscle was decellularized. The tissue was sliced to be ~2 mm thick and was rinsed with deionized water, then stirred in 1% sodium dodecyl sulfate (SDS) in PBS until decellularized. Decellularized tissue was then rinsed in deionized water to ensure removal of detergents. Pieces of decellularized tissue were sectioned and stained using hematoxylin and eosin to ensure removal of cells. Decellularized tissue was then lyophilized and milled to form a fine powder.

The skeletal muscle ECM was then digested in pepsin in low acid conditions, and then neutralized to physiologic or near physiologic pH through the addition of sodium hydroxide and 10×PBS. Neutralized skeletal muscle ECM solution was then diluted with PBS to the desired concentration of 6 mg/ml and allowed to gel in 96 well plates at 37° C. Successful gelation was confirmed by visual inspection of the material.

Solubilized native skeletal muscle ECM at a concentration of 6 mg/ml was successfully injected through a 25G needle into rat leg femoral muscle creating a gelled scaffold. Gelation occurred within 10-15 minutes. Muscle and ECM was excised and sectioned and stained using hematoxylin and eosin to confirm successful gelation of skeletal muscle ECM in the muscle.

Skeletal muscle ECM can also be used to deliver cells, such as skeletal myoblast or other muscle relevant cell types in the ECM.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of producing a composition comprising decellularized cardiac extracellular matrix comprising:
   (a) obtaining a cardiac tissue sample having an extracellular matrix component and non-extracellular matrix component;
   (b) processing the cardiac tissue sample to remove the non-extracellular matrix component to obtain decellularized cardiac extracellular matrix;
   (c) sterilizing the decellularized cardiac extracellular matrix; and
   (d) suspending and neutralizing said decellularized cardiac extracellular matrix in a saline buffered solution, wherein the decellularized extracellular matrix concentration in the composition is about 1 mg/ml to about 20 mg/ml.

2. The method of claim 1, wherein said method further comprises the step of lyophilizing and grinding up the decellularized cardiac extracellular matrix.

3. The method of claim 1, wherein said method further comprises the step of enzymatically treating the decellularized cardiac extracellular.

4. The method of claim 1, wherein in step (b) said decellularized cardiac extracellular matrix is digested with pepsin at a pH below 7.

5. The method of claim 1, wherein said composition can be injected through a high gauge needle into the myocardium.

6. The method of claim 1, wherein said composition spontaneously forms into a gel at body temperature.

7. The method of claim 1, wherein said composition further comprises cells, or other therapeutic agents.

8. The method of claim 1, wherein said composition is placed into tissue culture plates or wells, incubated at 37° C. to form into a gel.

9. The method of claim 1, further comprising a step of adjusting at least one of pH, salt concentration, and temperature of the composition.

10. The method of claim 5, wherein the needle is 22 gauge or higher.

11. The method of claim 1, wherein the decellularized extracellular matrix concentration in the composition is about 2 mg/ml to about 8 mg/ml.

12. The method of claim 1, further comprising processing the cardiac tissue sample with a detergent to remove the non-extracellular matrix component to obtain decellularized cardiac extracellular matrix.

13. The method of claim 12, wherein the detergent comprises SDS.

* * * * *

UNITED STATES PATENT AND TRADEMARK OFFICE
CERTIFICATE OF CORRECTION

PATENT NO. : 12,090,175 B2
APPLICATION NO. : 17/135785
DATED : September 17, 2024
INVENTOR(S) : Karen Christman et al.

Page 1 of 1

It is certified that error appears in the above-identified patent and that said Letters Patent is hereby corrected as shown below:

In the Specification

STATEMENT OF GOVERNMENT INTEREST, Column 1, Lines 19-22, delete:
"This invention was made with government support under grant No. OD004309 awarded by National Institutes of Health (NIH). The government has certain rights in the invention."

And insert:
--This invention was made with government support under OD004309 awarded by the National Institutes of Health. The government has certain rights in the invention.--

Signed and Sealed this
Tenth Day of February, 2026

John A. Squires
*Director of the United States Patent and Trademark Office*